US012043859B2

(12) United States Patent
Suominen et al.

(10) Patent No.: US 12,043,859 B2
(45) Date of Patent: Jul. 23, 2024

(54) RECOVERY, DECARBOXYLATION, AND PURIFICATION OF CANNABINOIDS FROM ENGINEERED CELL CULTURES

(71) Applicant: Genomatica, Inc., San Diego, CA (US)

(72) Inventors: Lauri H. Suominen, San Diego, CA (US); Jefferson Lievense, San Diego, CA (US); Aiguo Liu, San Diego, CA (US); Jorge Jesus Martinez-Gonzalez, San Diego, CA (US); Myong Kon Ko, San Diego, CA (US); Wei Nan, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 568 days.

(21) Appl. No.: 17/426,973

(22) PCT Filed: Jan. 30, 2020

(86) PCT No.: PCT/US2020/015904
§ 371 (c)(1),
(2) Date: Jul. 29, 2021

(87) PCT Pub. No.: WO2020/160284
PCT Pub. Date: Aug. 6, 2020

(65) Prior Publication Data
US 2022/0098625 A1    Mar. 31, 2022

Related U.S. Application Data

(60) Provisional application No. 62/934,371, filed on Nov. 12, 2019, provisional application No. 62/802,101, (Continued)

(51) Int. Cl.
*C12P 7/22* (2006.01)
*B01D 11/02* (2006.01)
*C12M 1/26* (2006.01)

(52) U.S. Cl.
CPC ............ *C12P 7/22* (2013.01); *B01D 11/0288* (2013.01); *B01D 11/0292* (2013.01); *C12M 33/10* (2013.01)

(58) Field of Classification Search
CPC ... C12P 7/22; B01D 11/0288; B01D 11/0292; C12M 33/10
See application file for complete search history.

(56) References Cited

U.S. PATENT DOCUMENTS 6,403,126 B1 *  6/2002  Webster ............... A61K 36/185
9,611,460 B2    4/2017  Page et al.
(Continued)

FOREIGN PATENT DOCUMENTS

WO    2011/017798 A1    2/2011
WO    2014/195521 A2    12/2014
(Continued)

OTHER PUBLICATIONS

Chemical Book, Cannabidiolic acid, https://www.chemicalbook.com/ChemicalProductProperty_EN_CB71365125.htm, last accessed Apr. 5, 2024 (Year: 2023).*
(Continued)

*Primary Examiner* — James H Alstrum-Acevedo
*Assistant Examiner* — Saleha Kuzniewski
(74) *Attorney, Agent, or Firm* — Kagan Binder, PLLC

(57) ABSTRACT

Methods of recovering cannabinoids from cell cultures include methods comprising steps of separating the cell culture at a temperature above the melting point of the cannabinoid to separate a light phase comprising liquid state cannabinoid from a heavy phase; and methods comprising treating the cell culture at a temperature below the melting point of the cannabinoid to separate a light phase from a heavy phase comprising solid state cannabinoid. Other methods include contacting the culture with a water-mis-
(Continued)

cible solvent to form a water-miscible phase and an aqueous phase, separating the two phases and recovering the cannabinoid. Other methods include contacting the culture with a water-immiscible solvent to form a water-immiscible phase and an aqueous phase, separating the two phases, and recovering the cannabinoid. Other methods include washing the inner surface of a fermentation vessel with alkaline solution to recover cannabinoid attached to the vessel surface. Various methods make use of aqueous solvent systems comprising no organic solvent, aqueous solvent systems comprising added water-miscible organic solvent, and dual-phase aqueous/water-immiscible solvent systems.

19 Claims, 5 Drawing Sheets

Related U.S. Application Data filed on Feb. 6, 2019, provisional application No. 62/798,909, filed on Jan. 30, 2019.

(56) References Cited

U.S. PATENT DOCUMENTS

| | | | |
|---|---|---|---|
| 9,822,384 | B2 | 11/2017 | Poulos et al. |
| 10,563,211 | B2* | 2/2020 | Keasling ............... C12N 15/81 |
| 11,685,908 | B2 | 6/2023 | Noble et al. |
| 2014/0141476 | A1 | 5/2014 | Page et al. |
| 2015/0128301 | A1 | 5/2015 | Page et al. |
| 2016/0010126 | A1* | 1/2016 | Poulos ...................... C12P 7/42 |
| 2017/0008870 | A1* | 1/2017 | Dibble .................. C07D 311/80 |
| 2017/0049830 | A1* | 2/2017 | Raderman ............ A61K 36/185 |
| 2017/0369913 | A1 | 12/2017 | Suominen et al. |
| 2018/0162828 | A1 | 6/2018 | Nadal Roura |
| 2018/0334692 | A1 | 11/2018 | Barr et al. |
| 2018/0371507 | A1 | 12/2018 | Poulos et al. |
| 2019/0002848 | A1 | 1/2019 | Gonzalez et al. |
| 2019/0010106 | A1* | 1/2019 | Oroskar et al. ....... C07C 37/685 |
| 2020/0224231 | A1 | 7/2020 | Hutagalung et al. |
| 2021/0189444 | A1* | 6/2021 | Alviar ...................... C12P 17/06 |
| 2021/0254030 | A1 | 8/2021 | Nobel et al. |
| 2021/0371884 | A1 | 12/2021 | Gonzalez et al. |
| 2022/0127649 | A1 | 4/2022 | Noble et al. |
| 2022/0177858 | A1 | 6/2022 | Noble et al. |
| 2022/0315969 | A1 | 10/2022 | Noble et al. |
| 2022/0347192 | A1 | 11/2022 | Noble et al. |
| 2023/0037234 | A1 | 2/2023 | Li et al. |
| 2023/0374473 | A1 | 11/2023 | Noble et al. |
| 2024/0052332 | A1 | 2/2024 | Noble et al. |

FOREIGN PATENT DOCUMENTS

| | | |
|---|---|---|
| WO | 2016/010827 A1 | 1/2016 |
| WO | 2017/139496 A1 | 8/2017 |
| WO | 2017/161041 A1 | 9/2017 |
| WO | 2017/181118 A1 | 10/2017 |
| WO | 2018/148848 A1 | 8/2018 |
| WO | 2018/148849 A1 | 8/2018 |
| WO | 2018/200888 A1 | 11/2018 |
| WO | 2018/204859 A1 | 11/2018 |
| WO | 2018/209143 A1 | 11/2018 |
| WO | 2019/014490 A1 | 1/2019 |
| WO | 2019/210404 A1 | 11/2019 |
| WO | 2020/028722 A1 | 2/2020 |
| WO | 2020/092823 A1 | 5/2020 |

OTHER PUBLICATIONS

Zirpel et al., Engineering yeasts as platform organisms for cannabinoid biosynthesis, 2017, Journal of Biotechnology, 259: 204-212 (Year: 2017).*

Carvalho et al., "Designing microorganisms for heterologous biosynthesis of cannabinoids," FEMS Yeast Research, vol. 17, No. 0, Jun. 2017, pp. 1-11.

Gagne, S.J., et al. (2012) "Identification of olivetolic acid cyclase from Cannabis sativa reveals a unique catalytic route to plant polyketides," Proceedings of the National Academy of Sciences of the United States of America (PNAS), 109:12811-12816 and Supporting Information 9 pp.

Kumano, T., et al. (2008) "Chemoenzymatic syntheses of prenylated aromatic small molecules using Streptomyces prenyltransferases with relaxed substrate specificities," Bioorganic & Medicinal Chemistry, 16:8117-8126.

Kuzuyama, T., et al., (2005) "Structural basis for the promiscuous biosynthetic prenylation of aromatic natural products," Nature, 435:983-987.

Muntendam, R., (2015) "Metabolomics and bioanalysis of terpenoid derived secondary metabolites," Analysis of *Cannabis sativa* L. metabolite production and prenylases for cannabinoid production, University of Groningen, Thesis, pp. 1-179. (Filed in 2 parts).

Schreckenbach, H.F. (2017) "Enzymatische Oligomerisierung von Alkendiphosphaten," Dissertation, zur Erlangung des akademischen Grades, doctor rerum naturalium (Dr. rer. Nat.) der Naturwissenschaftlichen Fakulatat II—Chemie und Physik der Martin-Luther-Universitat Halle-Wittenberg, pp. 159. (Dissertation in English) (Filed in 2 parts).

Tan, Z., et al., (2018) "Synthetic Pathway for the Production of Olivetolic Acid in Escherichia coli," ACS Synthetic Biology, 7:1886-1896.

Taura, F., et al. (2009) "Characterization of olivetol synthase, a polyketide synthase putatively involved in cannabinoid biosynthetic pathway," FEBS Letters, 583:2061-2066.

Valliere, M.A. (2019) "A cell-free platform for the prenylation of natural products and application to cannabinoid production," Nature Communications, 10:565:1-9.

Yang, Y. et al. (2012) "Catalytic Mechanism of Aromatic Prenylation by NphB," Biochemistry, 51:2606-2618 (NIH Author Manuscript 28 pages).

Yang, X., et al. (2016) "Structural basis for olivetolic acid formation by a polyketide cyclase from Cannabis sativa," The FEBS Journal, 283:1088-1106.

Zirpel, B. et al. (2017) "Engineering yeasts as platform organisms for cannabinoid biosynthesis," Journal of Biotechnology, 259:204-212.

* cited by examiner

RECOVERY, DECARBOXYLATION, AND PURIFICATION OF CANNABINOIDS FROM ENGINEERED CELL CULTURES

PRIORITY CLAIM

This application claims priority to International Application No. PCT/US2020/015904, filed Jan. 30, 2020, which claims the benefit of U.S. Provisional Patent Application Serial Nos. 62/798,909, filed Jan. 30, 2019, 62/802,101, filed Feb. 6, 2019, and 62/934,371, filed Nov. 12, 2019, all applications entitled Recovery, Decarboxylation, and Purification of Cannabinoids from Engineered Cell Cultures, wherein said applications are incorporated herein by reference in their entireties.

FIELD OF THE DISCLOSURE

This disclosure relates to the recovery, decarboxylation, and/or purification of a cannabinoid generated in a cell culture comprising cells engineered to produce the cannabinoid.

BACKGROUND OF THE DISCLOSURE

Cannabinoids are prenylated isoprenoids found naturally in the plant *Cannabis sativa*. Although cannabinoids have been used by humans for thousands of years, it is only in recent years that cannabinoids have been seriously studied for the treatment of a wide array of disorders including insomnia, chronic pain, epilepsy, and post-traumatic stress disorder (Babson et al. (2017) *Curr. Psychiatry Rep.* 19:23; Romero-Sandoval et al. (2017) *Curr. Rheumatol. Rep.* 19:67; O'Connell et al. (2017) *Epilepsy Behav.* 70:341-348; Zir-Aviv et al. (2016) *Behav. Pharmacol.* 27:561-569). A *Cannabis sativa* plant may contain over a hundred different cannabinoids which may have different physiological effects. For example, the cannabinoid tetrahydrocannabinol (THC) is responsible for the well-known psychotropic effects of *Cannabis* extracts, whereas cannabidiol (CBD) lacks these effects but has been demonstrated to reduce inflammation in multiple contexts. Purifying individual cannabinoid species from the *Cannabis sativa* plant is time-consuming and costly, and results in low yields of many cannabinoid species which may be present as only a small fraction of the total cannabinoid in the plant.

Engineering cells for the production of a specific cannabinoid or cannabinoid precursor would greatly increase the efficiency of obtaining particular cannabinoids. The use of engineered cell cultures for cannabinoid production presents a problem of recovering and purifying the cannabinoid from the cell culture. In addition, in the case of certain cannabinoids produced in acid form, it would be advantageous to accomplish decarboxylation in concert with recovery and purification.

SUMMARY OF THE DISCLOSURE

Briefly, the present disclosure provides a first method of recovering a cannabinoid from a cell culture, the method comprising: a) providing a cell culture comprising cells engineered to produce a cannabinoid in a culture medium; b) heating the culture to a temperature above the melting point of the cannabinoid; c) separating the culture to separate a first light phase comprising liquid-phase cannabinoid from a heavy phase comprising culture medium, cells, and insoluble and aqueous-soluble cellular components, wherein the separation is performed at a temperature above the melting point of the cannabinoid; and d) recovering the first light phase from the separated culture, wherein the first light phase comprises the cannabinoid. In embodiments, step c) of separation includes separation under g-force, which includes gravity settling, hydro cyclone, and centrifugation separations.

An alternate embodiment of this first method may comprise: a) providing a cell culture comprising cells engineered to produce a cannabinoid in a culture medium; b) separating the culture to provide a pellet comprising cells, insoluble cellular components, and cannabinoid, and a supernatant comprising culture medium; c) removing the supernatant; d) heating the pellet to a temperature above the melting point of the cannabinoid; e) separating the pellet to separate a first light phase comprising liquid-phase cannabinoid from a heavy phase comprising cells and insoluble and aqueous-soluble cellular components, wherein the separation is performed at a temperature above the melting point of the cannabinoid; and recovering the first light phase from the separated culture, wherein the first light phase comprises the cannabinoid. In embodiments, step b) of separating includes g-force separation or filtration of the culture; step e) of separation includes g-force separation, or combinations thereof.

In another aspect, the present disclosure provides a second method of recovering a cannabinoid from a cell culture, the method comprising: a) providing a cell culture comprising cells engineered to produce a cannabinoid in a culture medium; b) treating the culture at a temperature below the melting point of the cannabinoid to generate a first pellet comprising cells, insoluble cellular material, and the cannabinoid, and a first supernatant comprising culture medium; c) removing the first supernatant from the first pellet; d) adding a water-miscible organic solvent, to the first pellet to generate a solvent-extracted pellet mixture; e) treating the solvent-extracted pellet mixture to generate a second pellet and a second supernatant, wherein the second supernatant comprises the water-miscible organic solvent, water, and the cannabinoid; and f) recovering the second supernatant comprising the cannabinoid. In embodiments, step b) of treating includes separation under g-force, evaporation, flocculation, or filtration of the culture; in step d) or adding the water-miscible organic solvent uses a C1-C4 alcohol, acetonitrile, acetone, dimethyl sulfoxide, or combination thereof; step e) of treating includes g-force separating or filtrating the solvent-extracted pellet mixture.

In another aspect, the present disclosure provides a third method of recovering a cannabinoid from a cell culture, the method comprising: a) providing a cell culture comprising cells engineered to produce a cannabinoid in a culture medium; b) treating the culture at a temperature below the melting point of the cannabinoid to generate a first pellet comprising cells, insoluble cellular material, and the cannabinoid, and a first supernatant comprising culture medium; c) removing the first supernatant from the first pellet; d) adding a water-immiscible organic solvent, o the first pellet to generate a solvent-extracted pellet mixture; e) separating the solvent-extracted pellet mixture to generate a heavy phase and a light phase, wherein the light phase comprises the water-immiscible organic solvent and the cannabinoid; and f) recovering the light phase comprising the cannabinoid. In embodiments, step b) of treating includes separation under g-force, evaporation, flocculation, or filtration of the culture; in step d) or adding the water-miscible organic solvent uses an acetate, a hydrocarbon, a natural or synthetic oil, or an alcohols having 5 or more carbon atoms, or combination thereof; step e) of separating includes g-force separating the solvent-extracted pellet mixture.

In another aspect, the present disclosure provides a fourth method of recovering a cannabinoid from a cell culture, the method comprising: a) providing a cell culture comprising cells engineered to produce a cannabinoid in a culture medium; b) contacting the culture with a water-immiscible solvent, wherein the contacting forms a water-immiscible phase and an aqueous phase in the culture medium; c) separating the water-immiscible phase from the aqueous phase, wherein the water-immiscible phase comprises the cannabinoid; and d) recovering the cannabinoid from the water-immiscible phase. In embodiments, step c) of separating includes g-force separation of the water-immiscible phase.

In another aspect, the present disclosure provides a fifth method of recovering a cannabinoid from a cell culture, the method comprising: a) providing a cell culture comprising cells engineered to produce a cannabinoid in a culture medium; b) contacting the culture with a water-miscible organic solvent, wherein the contacting forms a solvent extraction mixture comprising the water-miscible organic solvent, water, and the cannabinoid and culture medium; c) treating the solvent-extracted culture mixture to generate a pellet and a supernatant, wherein the supernatant comprises the water-miscible organic solvent, water, and the cannabinoid; and d) recovering the supernatant comprising the cannabinoid. In embodiments, step c) of treating includes g-force separation or filtration of the culture; step e) of separation includes g-force separation, or combinations thereof.

Aspects of the second, third, fourth and fifth method can optionally include adding a filter aid (e.g., silica, diatomaceous earth, cellulosic material, etc.) to the cell culture or the solvent-extracted pellet mixture prior to, or during the filtration step. In some aspects, a filtration membrane having a normal pore size in the range of 0.2 micrometer to 20 micrometer is used. In some aspects, the retentate is contacted with an amount of solvent to provide a weight ratio of retentate:solvent in the range of 2:1 to 1:20, 1:1 to 1:10, or 1:1.5 to 1:5. In some aspects, the solvent comprises ethanol. In some aspects, the method further comprises a step of separating the retentate and solvent, such as by g-force, to form a liquid phase comprising the solvent and cannabinoid and a heavy phase comprising semi-solids, solids, or a mixture thereof.

In another aspect, the present disclosure provides a sixth method of recovering a cannabinoid from a cell culture, the method comprising: a) removing a cell culture from a fermentation vessel, the cell culture comprising cells engineered to produce a cannabinoid in a culture medium, wherein the fermentation vessel comprises a surface that contacts the cannabinoid in the culture medium; and b) contacting the surface of the fermentation vessel with an alkaline solution, wherein contacting removes cannabinoid from the surface.

Aspects of the sixth method can optionally include using an alkali metal hydroxide (such as NaOH and/or KOH), an alkaline earth metal hydroxide, or a combination thereof, in the alkaline solution, such as at a concentration of about 0.1N or greater, 0.2N or greater, 0.25N or greater, 0, 3N or greater, 0.4N or greater, 0.5N or greater, 0.6N or greater, 0.7N or greater, 0.8N or greater, 0.9N or greater, 1N or greater, 1.5N or greater, 1.75N or greater, 2N or greater, 2.5N or greater, 2.75N or greater, or 3N or greater. In some aspects, contacting is performed at a temperature of about 25° C. or greater, about 30° C. or greater, about 35° C. or greater, about 40° C. or greater, about 45° C. or greater, about 50° C. or greater, about 55° C. or greater, about 60° C. or greater, about 65° C. or greater, about 70° C. or greater, about 75° C. or greater, about 80° C. or greater, about 85° C. or greater, about 90° C. or greater, about 95° C. or greater, or about 100° C. or greater. In some aspects a step of neutralizing the alkaline solution comprising the cannabinoid, such as with an inorganic or organic acid, is performed.

The method can also further include a step of contacting the acid-neutralized solution with a water immiscible solvent in order to extract the cannabinoid from the solution to the solvent.

The preceding summary of the present disclosure is not intended to describe each embodiment of the present invention. The details of one or more embodiments of the invention are also set forth in the description below. Other features, objects, and advantages of the invention will be apparent from the description and from the claims.

In this application:
"cannabinoid" or "cannabinoid compound" as used herein refers to a member of a class of unique meroterpenoids found until now primarily in *Cannabis sativa*; and
"cellular material" refers to living or formerly living cells or fragments thereof such as cells of bacteria, archaea, or eukaryotes, including yeast, algae, and the like.

All scientific and technical terms used herein have meanings commonly used in the art unless otherwise specified.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising," and the like.

DETAILED DESCRIPTION

Figure 1:
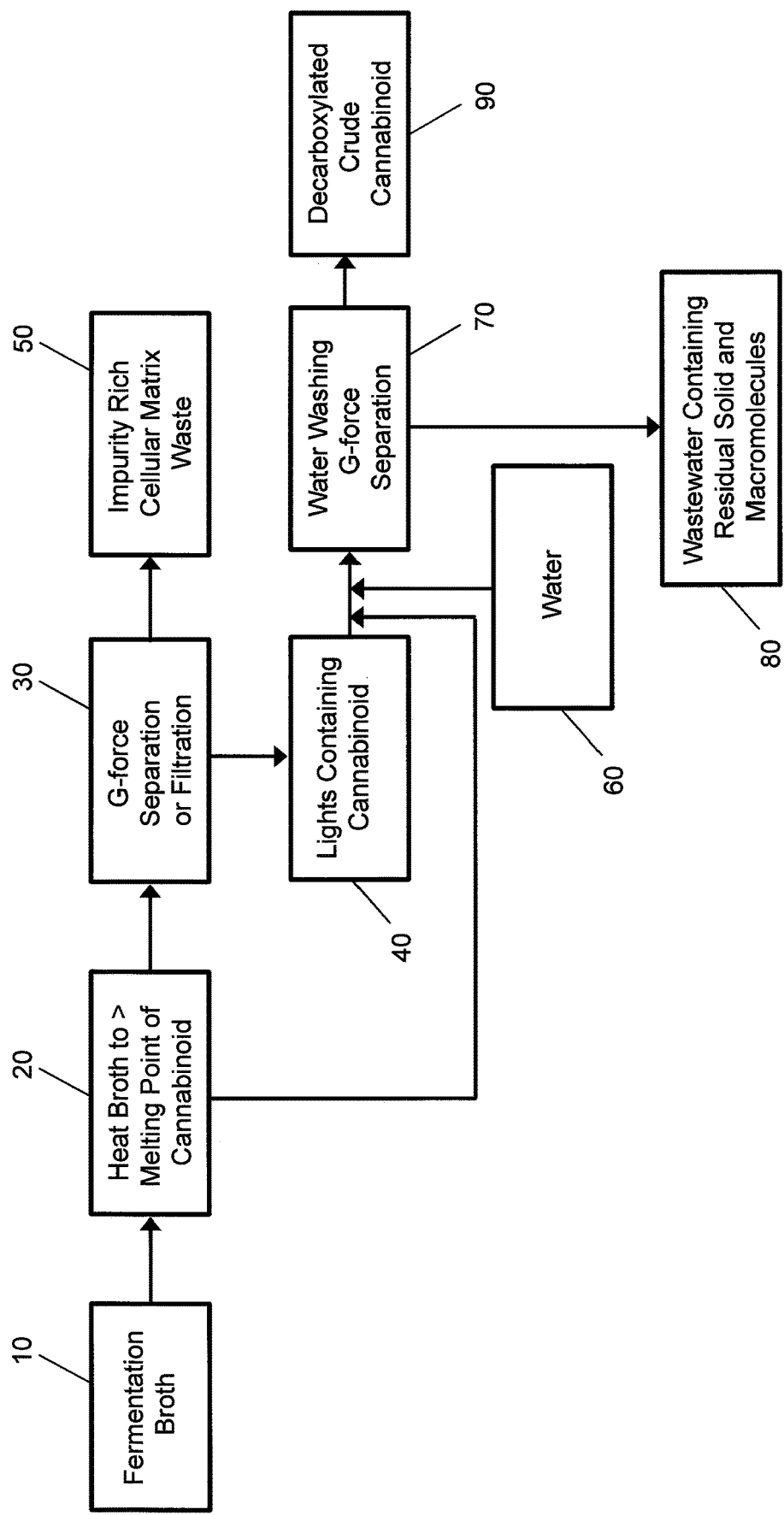
FIG. 1 is a flow chart for a process of recovery and purification of a cannabinoid from an engineered cell culture, as described in Example 1 herein.

The present disclosure provides methods of recovery, decarboxylation, and/or purification of a cannabinoid generated in a cell culture comprising cells engineered to produce the cannabinoid.

Any suitable cannabinoids or subset of cannabinoids may be recovered, purified, or (where applicable) decarboxylated by the methods of the present disclosure, including those listed above in the definition of "cannabinoid", including any subset thereof, and including those disclosed in WO 2017/181118; WO 2018/204859; WO 2018/200888; US 9,822,384; WO 2017/139496; WO 2018/148848; WO 2018/148849; US 2018/0371507; WO 2018/209143; and co-assigned provisional patent application titled "Engineered Cells for Improved Production of Cannabinoids" filed on even date herewith; each of which is incorporated herein by reference.

The terms "cannabinoid", "cannabinoid product", and "cannabinoid compound" or "cannabinoid molecule" are used herein to refer to a member of a class of meroterpenoids that are naturally-occurring in Cannabis sativa. As used herein, the terms "cannabinoid", "cannabinoid product", and "cannabinoid compound" or "cannabinoid molecule" are used interchangeably to refer a molecule containing a polyketide moiety, e.g., olivetolic acid or another 2-alkyl-4,6-dihydroxybenzoic acid, and a terpene-derived moiety e.g., a geranyl group. Geranyl groups are derived from the diphosphate of geraniol, known as geranyl-diphosphate or geranyl-pyrophosphate that forms the acidic cannabinoid cannabigerolic acid (CBGA). In some embodiments, cannabinoids can optionally be converted to increase their bioactivity by enzymatic treatment (e.g., by decarboxylation via enzyme treatment in vivo or in vitro to form the neutral cannabinoid) and chemically (e.g., decarboxylating to form a neutral cannabinoid by heating). Natural cannabinoid decarboxylation in the plant can also occur spontaneously.

The term cannabinoid includes acid cannabinoids and neutral cannabinoids. The term cannabinoids also includes derivatives of naturally-occurring cannabinoids, such as, but not limited to, cannabinoids having different alkyl chain lengths of side groups than are found in naturally-occurring cannabinoids. The term "acidic cannabinoid" generally refers to a cannabinoid having a carboxylic acid moiety. The carboxylic acid moiety may be present in protonated form (i.e., as —COOH) or in deprotonated form (i.e., as carboxylate —COO$^-$). Examples of acidic cannabinoids include, but are not limited to, cannabigerolic acid, cannabidiolic acid, and $\Delta^9$-tetrahydrocannabinolic acid. The term "neutral cannabinoid" refers to a cannabinoid that does not contain a carboxylic acid moiety (i.e., does contain a moiety —COOH or —COO$^-$). Examples of neutral cannabinoids include, but are not limited to, cannabigerol, cannabidiol, and $\Delta^9$-tetrahydrocannabinol.

Throughout the applications, abbreviated terms may be used to designate cannabinoids and related molecules. For example, the term "CBGA" refers to cannabigerolic acid, "OA" refers to olivetolic acid; "CBG" refers to cannabigerol; "CBDA" refers to cannabidiolic acid; "CBD" refers to cannabidiol; "THC" refers to $\Delta^9$-tetrahydrocannabinol ($\Delta^9$-THC); "$\Delta$8-THC" refers to $\Delta$8-tetrahydrocannabinol; "THCA" refers to $\Delta^9$-tetrahydrocannabinolic acid ($\Delta^9$-THCA); "$\Delta$8-THCA" refers to $\Delta$8-tetrahydrocannabinolic acid; "CBCA" refers to cannabichromenic acid; "CBC" refers to cannabichromene; "CBN" refers to cannabinol; "CBDN" refers to cannabinodiol; "CBNA" refers to eannabinolic acid; "CBV" refers to cannabivarin; "CBVA" refers to cannabivarinic acid; "THCV" refers to $\Delta^9$-tetrahydrocannabivarin ($\Delta^9$9-THCV); "$\Delta$8-THCV" refers to "$\Delta$8-tetrahydrocannabivarin; "THCVA" refers to $\Delta^9$-tetrahydrocannabivarinic acid ($\Delta^9$-THCV); "$\Delta$8-THCVA" refers to $\Delta$8-tetrahydrocannabivarinic acid; "CBGV" refers to cannabigerovarin; "CBGVA" refers to cannabigerovarinic acid; "CBCV" refers to cannabichromevarin; "CBCVA" refers to cannabichromevarinic acid; "CBDV" refers to cannabidivarin; "CBDVA" refers to cannabidivarinic acid; "MPF" refers to multiple precursor feeding; "PKS" refers to a polyketide synthase; "GOT" refers to geranyl pyrophosphate olivetolate geranyl transferase; and "HPLC" refers to high performance liquid chromatography.

Cannabinoids may include, but are not limited to, cannabichromene (CBC) type (e.g. cannabichromenic acid), cannabigerol (CBG) type (e.g. cannabigerolic acid), cannabidiol (CBD) type (e.g. cannabidiolic acid), $\Delta^9$-trans-tetrahydrocannabinol ($\Delta^9$-THC) type (e.g. $\Delta^9$-tetrahydrocannabinolic acid), $\Delta^8$-trans-tetrahydrocannabinol ($\Delta^8$-THC) type, cannabicyclol (CBL) type, cannabielsoin (CBE) type, cannabinol (CBN) type, cannabinodiol (CBND) type, cannabitriol (CBT) type, cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CBD), cannabidiol monomethylether (CBDM), cannabidiol-C$_4$ (CBD-C$_4$), cannabidivarinic acid (CBDVA), cannabidivarin (CBDV), cannabidiorcol (CBD-C$_1$), $\Delta^9$-tetrahydrocannabinolic acid A (THCA-A), $\Delta^9$-tetrahydrocannabinolic acid B (THCA-B), $\Delta^9$-tetrahydrocannabinol (THC), $\Delta^9$-tetrahydrocannabinolic acid-C$_4$ (THCA-C$_4$), $\Delta^9$-tetrahydrocannabinol-C$_4$ (THC-C$_4$), $\Delta^9$-tetrahydrocannabivarinic acid (THCVA), $\Delta^9$-tetrahydrocannabivarin (THCV), $\Delta^9$-tetrahydrocannabiorcolic acid (THCA-C$_1$), $\Delta^9$-tetrahydrocannabiorcol (THC-C$_1$), $\Delta^7$-cis-iso-tetrahydrocannabivarin, $\Delta^8$-tetrahydrocannabinolic acid ($\Delta^8$-THCA), $\Delta^8$-tetrahydrocannabinol ($\Delta^8$-THC), cannabicyclolic acid (CBLA), cannabicyclol (CBL), cannabicyclovarin (CBLV), cannabielsoic acid A (CBEA-A), cannabielsoic acid B (CBEA-B), cannabielsoin (CBE), cannabielsoinic acid, cannabicitranic acid, cannabinolic acid (CBNA), cannabinol (CBN), cannabinol methylether (CBNM), cannabinol-C$_4$, (CBN-C$_4$), cannabivarin (CBV), cannabinol-C$_2$ (CNB-C$_2$), cannabiorcol (CBN-C$_1$), cannabinodiol (CBND), cannabinodivarin (CBVD), cannabitriol (CBT), 10-ethyoxy-9-hydroxy-delta-6a-tetrahydrocannabinol, 8,9-dihydroxyl-delta-6a-tetrahydrocannabinol, cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxy-alpha-alpha-2-trimethyl-9-n-propyl-2,6-methano-2H-1-benzoxocin-5-methanol (OH-iso-HHCV), cannabiripsol (CBR), and trihydroxy-delta-9-tetrahydrocannabinol (triOH-THC).

Cannabinoid compounds of interest include, without limitation, CBG, CBDA, CBD, THC, $\Delta$8-THC, THCA, $\Delta$8-THCA, CBCA, CBA, CBN, CBDN, CBNA, CBV, CBVA, THCV, THCVA, $\Delta$8-THCA, CBGV, CBGVA, CBCV, CBCVA, CBDV and CBDVA and derivatives thereof. Given the high levels of products obtained using the novel manufacturing systems created by the present invention, also of interest are some less well-studied cannabinoids that may have more potent and selective activities in various human medical conditions. They include, without limitation, the cannabichromanones, cannabicoumaronone, cannabicitran, 10-oxo-A$^{6a}$(10a)-tetrahydrohydrocannabinol (OTHC), cannabiglendol, and $\Delta$7-isotetrahydrocannabinol.

Any suitable culture of cells engineered to produce a cannabinoid may be used in the methods of the present disclosure, including those described in WO 2018/204859; WO 2018/200888; and co-assigned U.S. provisional and international patent applications titled "Engineered Cells for Improved Production of Cannabinoids" (Ser. No. 62/798,926, filed Jan. 31, 2019; and Ser. No. 62/802,085, filed Feb. 6, 2019; and corresponding international patent application), each of which is incorporated herein by reference. The cells engineered to produce a cannabinoid (host cells) may be of any suitable biological type, which may include bacterial cells, fungal cells or algal cells. In various embodiments, cells engineered to produce a cannabinoid may produce the cannabinoid internally, may secrete the cannabinoid, may produce enzymes that produce cannabinoids ex vivo, or other arrangements whereby the cells directly or indirectly produce a cannabinoid.

A host cell as provided herein can be a prokaryotic cell or a eukaryotic cell. Eukaryotic cells may be microbial eukaryotic cells, such as, for example, fungal cells or microalgal cells. Further, a eukaryotic cell engineered to produce at least one cannabinoid can be a cell or cell line derived from a multicellular eukaryote, such as but not limited to an alga, moss, or higher plant. Prokaryotic cells that can be engineered as provided herein include bacterial cells, archaebacterial cells, and cyanobacterial cells.

In some embodiments, a host cell is a microorganism such as a bacterium, filamentous fungus, or yeast. Hosts can be selected based on their ability to take up and utilize particular carbon sources, nitrogen sources, or precursor molecules or may be engineered to take up and utilize molecules that may be added to the culture medium.

Nonlimiting examples of suitable microbial hosts for the bio-production of a cannabinoid include, but are not limited to, any gram negative organisms, more particularly a member of the family Enterobacteriaceae, such as *E. coli*, or *Oligotropha carboxidovorans*, or a *Pseudomononas* sp.; any gram positive microorganism, for example *Bacillus subtilis*, *Lactobaccilus* sp. or *Lactococcus* sp.; a yeast, for example *Saccharomyces cerevisiae*, *Pichia pastoris* or *Pichia stipitis*; and other groups or microbial species. More particularly, suitable microbial hosts for the bio-production of olivetolic acid or at least one cannabinoid generally include, but are not limited to, members of the genera *Clostridium*, *Zymomonas*, *Escherichia*, *Salmonella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, *Brevibacterium*, *Pichia*, *Candida*, *Hansenula*, and *Saccharomyces*. Hosts that may be particularly of interest include: *Oligotropha carboxidovorans* (such as strain OM5), *Escherichia coli*, *Alcaligenes eutrophus* (*Cupriavidus necator*), *Bacillus licheniformis*, *Paenibacillus macerans*, *Rhodococcus erythropolis*, *Pseudomonas putida*, *Lactobacillus plantarum*, *Enterococcus faecium*, *Enterococcus gallinarium*, *Enterococcus faecalis*, *Bacillus subtilis* and *Saccharomyces cerevisiae*.

A variety of microorganisms may be suitable for the production of cannabinoids in cell culture. Such organisms include both prokaryotic and eukaryotic organisms including, but not limited to, bacteria, including archaea and eubacteria, and eukaryotes, including yeast, plant, insect, animal, and mammal, including human. Exemplary species are reported in U.S. application Ser. No. 13/975,678 (filed Aug. 26, 2013), which is incorporated herein by reference, and include, for example, *Escherichia coli*, *Saccharomyces cerevisiae*, *Saccharomyces kluyveri*, *Candida boidinii*, *Clostridium kluyveri*, *Clostridium acetobutylicum*, *Clostridium beijerinckii*, *Clostridium saccharoperbutylacetonicum*, *Clostridium perfringens*, *Clostridium difficile*, *Clostridium botulinum*, *Clostridium tyrobutyricum*, *Clostridium tetanomorphum*, *Clostridium tetani*, *Clostridium propionicum*, *Clostridium aminobutyricum*, *Clostridium subterminale*, *Clostridium sticklandii*, *Ralstonia eutropha*, *Mycobacterium bovis*, *Mycobacterium tuberculosis*, *Porphyromonas gingivalis*, *Arabidopsis thaliana*, *Thermus thermophilus*, *Pseudomonas* species, including *Pseudomonas aeruginosa*, *Pseudomonas putida*, *Pseudomonas stutzeri*, *Pseudomonas fluorescens*, *Homo sapiens*, *Oryctolagus cuniculus*, *Rhodobacter spaeroides*, *Thermoanaerobacter brockii*, *Metallosphaera sedula*, *Leuconostoc mesenteroides*, *Chloroflexus aurantiacus*, *Roseiflexus castenholzii*, *Erythrobacter*, *Simmondsia chinensis*, *Acinetobacter* species, including *Acinetobacter calcoaceticus* and *Acinetobacter baylyi*, *Porphyromonas gingivalis*, *Sulfolobus tokodaii*, *Sulfolobus solfataricus*, *Sulfolobus acidocaldarius*, *Bacillus subtilis*, *Bacillus cereus*, *Bacillus megaterium*, *Bacillus brevis*, *Bacillus pumilus*, *Rattus norvegicus*, *Klebsiella pneumonia*, *Klebsiella oxytoca*, *Euglena gracilis*, *Treponema denticola*, *Moorella thermoacetica*, *Thermotoga maritima*, *Halobacterium salinarum*, *Geobacillus stearothermophilus*, *Aeropyrum pernix*, *Sus scrofa*, *Caenorhabditis elegans*, *Corynebacterium glutamicum*, *Acidaminococcus fermentans*, *Lactococcus lactis*, *Lactobacillus plantarum*, *Streptococcus thermophilus*, *Enterobacter aerogenes*, *Candida*, *Aspergillus terreus*, *Pediococcus pentosaceus*, *Zymomonas mobilis*, *Acetobacter pasteurians*, *Kluyveromyces lactis*, *Eubacterium barkeri*, *Bacteroides capillosus*, *Anaerotruncus colihominis*, *Natranaerobius thermophilusm*, *Campylobacter jejuni*, *Haemophilus influenzae*, *Serratia marcescens*, *Citrobacter amalonaticus*, *Myxococcus xanthus*, *Fusobacterium nuleatum*, *Penicillium chrysogenum*, marine gamma proteobacterium, butyrate-producing bacterium, *Nocardia iowensis*, *Nocardia farcinica*, *Streptomyces griseus*, *Schizosaccharomyces pombe*, *Geobacillus thermoglucosidasius*, *Salmonella typhimurium*, *Vibrio cholera*, *Heliobacter pylori*, *Nicotiana tabacum*, *Oryza sativa*, *Haloferax mediterranei*, *Agrobacterium tumefaciens*, *Achromobacter denitrificans*, *Fusobacterium nucleatum*, *Streptomyces clavuligenus*, *Acinetobacter baumanii*, *Mus musculus*, *Lachancea kluyveri*, *Trichomonas vaginalis*, *Trypanosoma brucei*, *Pseudomonas stutzeri*, *Bradyrhizobium japonicum*, *Mesorhizobium loti*, *Bos taurus*, *Nicotiana glutinosa*, *Vibrio vulnificus*, *Selenomonas ruminantium*, *Vibrio parahaemolyticus*, *Archaeoglobus fulgidus*, *Haloarcula marismortui*, *Pyrobaculum aerophilum*, *Mycobacterium smegmatis* MC2 155, *Mycobacterium avium* subsp. *paratuberculosis* K-10, *Mycobacterium marinum* M, *Tsukamurella paurometabola* DSM 20162, *Cyanobium* PCC7001, *Dictyostelium discoideum* AX4, as well as other exemplary species disclosed herein or available as source organisms for corresponding genes.

In certain embodiments, suitable organisms include *Acinetobacter baumannii* Naval-82, *Acinetobacter* sp. ADP1, *Acinetobacter* sp. strain M-1, *Actinobacillus succinogenes* 130Z, *Allochromatium vinosum* DSM 180, *Amycolatopsis methanolica*, *Arabidopsis thaliana*, *Atopobium parvulum* DSM 20469, *Azotobacter vinelandii* DJ, *Bacillus alcalophilus* ATCC 27647, *Bacillus azotoformans* LMG 9581, *Bacillus coagulans* 36D1, *Bacillus megaterium*, *Bacillus methanolicus* MGA3, *Bacillus methanolicus* PB1, *Bacillus methanolicus* PB-1, *Bacillus selenitireducens* MLS10, *Bacillus smithii*, *Bacillus subtilis*, *Burkholderia cenocepacia*, *Burkholderia cepacia*, *Burkholderia multivorans*, *Burkholderia pyrrocinia*, *Burkholderia stabilis*, *Burkholderia thailandensis* E264, *Burkholderiales bacterium* Joshi_001, Butyrate-producing bacterium L2-50, *Campylobacter jejuni*, *Candida albicans*, *Candida boidinii*, *Candida methylica*, *Carboxydothermus hydrogenoformans*, *Carboxydothermus hydrogenoformans* Z-2901, *Caulobacter* sp. AP07, *Chloroflexus aggregans* DSM 9485, *Chloroflexus aurantiacus* J-10-fl, *Citrobacter freundii*, *Citrobacter koseri* ATCC BAA-895, *Citrobacter youngae*, *Clostridium*, *Clostridium* acetobutylicum, Clostridium acetobutylicum ATCC824, Clostridium acidurici, Clostridium aminobutyricum, Clostridium asparagiforme DSM 15981, Clostridium beijerinckii, Clostridium beijerinckii NCIMB 8052, Clostridium bolteae ATCC BAA-613, Clostridium carboxidivorans P7, Clostridium cellulovorans 743B, Clostridium difficile, Clostridium hiranonis DSM 13275, Clostridium hylemonae DSM 15053, Clostridium kluyveri, Clostridium kluyveri DSM 555, Clostridium ljungdahli, Clostridium ljungdahlii DSM 13528, Clostridium methylpentosum DSM 5476, Clostridium pasteurianum, Clostridium pasteurianum DSM 525, Clostridium perfringens, Clostridium perfringens ATCC13124, Clostridium perfringens str. 13, Clostridium phytofermentans ISDg, Clostridium saccharobutylicum, Clostridium saccharoperbutylacetonicum, Clostridium saccharoperbutylacetonicum N1-4, Clostridium tetani, Corynebacterium glutamicum ATCC14067, Corynebacterium glutamicum R, Corynebacterium sp. U-96, Corynebacterium variabile, Cupriavidus necator N-1, Cyanobiurn PCC7001, Desulfatibacillum alkenivorans AK-01, Desulfitobacteriurn hafniense, Desulfitobacterium metallireducens DSM 15288, Desulfotomaculum reducens MI-1, Desulfovibrio africanus str. Walvis Bay, Desulfovibrio fructosovorans JJ, Desulfovibrio vulgaris str. Hildenborough, Desulfovibrio vulgaris str. 'Miyazaki F', Dictyostelium discoideum AX4, Escherichia coli, Escherichia coli; K-12, Escherichia coli K-12 MG1655, Eubacterium hallii DSM 3353, Flavobacterium frigoris, Fusobacterium nucleatum subsp. polymorphum ATCC10953, Geobacillus sp. Y4.1MC1, Geobacillus themodenitrificans NG80-2, Geobacter bemidjiensis Bem, Geobacter sulfurreducens, Geobacter sulfurreducens PCA, Geobacillus stearothermophilus DSM 2334, Haemophilus influenzae, Helicobacter pylori, Homo sapiens, Hydrogenobacter thermophilus, Hydrogenobacter thermophilus TK-6, Hyphomicrobium denitrificans ATCC51888, Hyphomicrobium zavarzinii, Klebsiella pneumoniae, Klebsiella pneumoniae subsp. pneumoniae MGH 78578, Lactobacillus brevis ATCC367, Leuconostoc rnesenteroides, Lysinibacillus fusiformis, Lysinibacillus sphaericus, Mesorhizobium loti MAFF303099, Metallosphaera sedula, Methanosarcina acetivorans, Methanosarcina acetivorans C2A, Methanosarcina barkeri, Methanosarcina mazei Tuc01, Methylobacter marinus, Methylobacterium extorquens, Methylobacterium extorquens AM1, Methylococcus capsulatas, Methylomonas aminofaciens, Moorella thermoacetica, Mycobacter sp. strain JC1 DSM 3803, Mycobacterium avium subsp. paratuberculosis K-10, Mycobacterium bovis BCG, Mycobacterium gastri, Mycobacterium marinum M, Mycobacterium smegmatis, Mycobacterium smegmatis MC2 155, Mycobacterium tuberculosis, Nitrosopumilus salaria BD31, Nitrososphaera gargensis Ga9.2, Nocardia farcinica IFM 10152, Nocardia iowensis (sp. NRRL 5646), Nostoc sp. PCC7120, Ogataea angusta, Ogataea parapolymorpha DL-1 (Hansenula polymorpha DL-1), Paenibacillus peoriae KCTC3763, Paracoccus denitrificans, Penicillium chrysogenum, Photobacterium profundum 3TCK, Phytofermentans ISDg, Pichia pastoris, Picrophilus torridus DSM9790, Porphyromonas gingivalis, Porphyromonas gingivalis W83, Pseudomonas aeruginosa PA01, Pseudomonas denitrificans, Pseudomonas knackmussii, Pseudomonas putida, Pseudomonas sp, Pseudomonas syringae pv. syringae B728a, Pyrobaculum islandicum DSM 4184, Pyrococcus abyssi, Pyrococcus furiosus, Pyrococcus horikoshii OT3, Ralstonia eutropha, Ralstonia eutropha H16, Rhodobacter capsulatus, Rhodobacter sphaeroides, Rhodobacter sphaeroides ATCC17025, Rhodopseudomonas palustris, Rhodopseudomonas palustris CGA009, Rhodopseudomonas palustris DX-1, Rhodospirillum rubrum, Rhodospirillum rubrum ATCC11170, Ruminococcus obeum ATCC29174, Saccharomyces cerevisiae, Saccharomyces cerevisiae S288c, Salmonella enterica, Salmonella enterica subsp. enterica serovar Typhimurium str. LT2, Salmonella enterica typhimurium, Salmonella typhimurium, Schizosaccharomyces pombe, Sebaldella termitidis ATCC33386, Shewanella oneidensis MR-1, Sinorhizobium meliloti 1021, Streptomyces coelicolor, Streptomyces griseus subsp. griseus NBRC13350, Sulfolobus acidocalarius, Sulfolobus solfataricus P-2, Synechocystis str. PCC6803, Syntrophobacter fumaroxidans, Thauera aromatica, Thermoanaerobacter sp. X514, Thermococcus kodakaraensis, Thermococcus litoralis, Thermoplasma acidophilum, Thermoproteus neutrophilus, Thermotoga maritima, Thiocapsa roseopersicina, Tolumonas auensis DSM 9187, Trichomonas vaginalis G3, Trypanosoma brucei, Tsukamurella paurometabola DSM 20162, Vibrio cholera, Vibrio harveyi ATCC BAA-1116, Xanthobacter autotrophicus Py2, Yersinia intermedia, or Zea mays.

Algae that can be engineered for cannabinoid production include, but are not limited to, unicellular and multicellular algae. Examples of such algae can include a species of rhodophyte, chlorophyte, heterokontophyte (including diatoms), tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species that are considered for cannabinoid production include, but are not limited to, Neochloris oleoabundans, Scenedesmus dimorphus, Euglena gracilis, Phaeodactylum tricornutum, Pleurochrysis carterae, Prymnesium parvum, Tetraselmis chui, Nannochloropsis gaditiana. Dunaliella salina. Dunaliella tertiolecta, Chlorella vulgaris, Chlorella variabilis, and Chlamydomonas reinhardtii. Additional or alternate algal sources can include one or more microalgae of the Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrsosphaera, Cricosphaera, Crypthecodinium, Cryptomonas, Cyclotella, Dunaliella, Ellipsoidon, Emiliania. Eremosphaera, Ernodesmius, Euglena, Franceia, Fragilaria, Gloeolhamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus. Platymonas, Pleurochrsis, Pleurococcus, Prototheca, Pseudochlorella, Pyramimonas, Pvrobotrys, Scenedesmus, Skeletonema, Spyrogyra, Stichococcus, Tetraselmis, Thalassiosira, Viridiella, and Volvox species, and/or one or more cyanobacteria of the Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylcoccopsis, Dermocarpella, Fischerella, Fremyella, Geitleria, Geitlerinema, Gloeobacter, Gloeocapsa, Gloeothece, Halospirulina, Ivengariella, Leptolyngbya, Limnothrix, Lyngbya, Microcoleus, Microcystis, Mxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scvtonema, Spirulina, Stanieria, Starria,

*Stigonema, Symploca, Synechococcus, Synechocystis, Tolipothrix, Trichodesmium, Tychonema*, and *Xenococcus* species.

The ability to genetically modify the host is essential for any recombinant production system. The mode of gene transfer technology may be by electroporation, conjugation, transduction or natural transformation. A broad range of host conjugative plasmids and drug resistance markers are available. The cloning vectors are tailored to the host organisms based on the nature of antibiotic resistance markers that can function in that host.

Depending on the desired microorganism or strain to be used, the appropriate culture medium may be used. For example, descriptions of various culture media may be found in "Manual of Methods for General Bacteriology" of the American Society for Bacteriology (Washington D.C., USA, 1981). As used here, culture medium, or simply "medium" as it relates to the growth source refers to the starting medium be it in a solid or liquid form. "Cultured medium", on the other hand and as used here refers to medium (e.g. liquid medium) containing microbes that have been fermentatively grown and can include other cellular biomass. The medium generally includes one or more carbon sources, nitrogen sources, inorganic salts, vitamins and/or trace elements. "Whole culture" as used herein refers to cultured cells plus the culture medium they are cultured in and any products or byproducts produced by the cells.

Exemplary carbon sources include sugar carbons such as sucrose, glucose, galactose, fructose, mannose, isomaltose, xylose, pannose, maltose, arabinose, cellobiose and 3-, 4-, or 5-oligomers thereof. Other carbon sources include alcohol and acid carbon sources such as methanol, ethanol, glycerol, formate and fatty acids. Still other carbon sources include carbon sources from gas such as synthesis gas, waste gas, methane, CO, $CO_2$ and any mixture of CO, $CO_2$ with $H_2$. Other carbon sources can include renewable feedstocks and biomass. Exemplary renewable feedstocks include cellulosic biomass, hemicellulosic biomass and lignin feedstocks.

In some embodiments, culture conditions include anaerobic growth or maintenance conditions. Exemplary anaerobic conditions have been described previously and are well known in the art. Exemplary anaerobic conditions for fermentation processes are disclosed, for example, in U.S. Patent Application Publication No 2009/0047719, filed Aug. 10, 2007. Any of these conditions can be employed with the microbial organisms as well as other anaerobic conditions well known in the art.

In some embodiments, culture conditions include aerobic or microaerobic growth or maintenance conditions. Exemplary aerobic conditions have been described previously and are well known in the art.

The culture conditions can include, for example, liquid culture procedures as well as fermentation and other large-scale culture procedures. Useful yields of the products can be obtained under anaerobic, aerobic, or microaerobic culture conditions.

Algae can be cultured photoautotrophically, without a reduced carbon source that can be used for energy, mixotrophically, where the algae are exposed to light that allows photosynthesis, and heterotrophically, where the cells rely entirely on a reduced carbon source provided in the culture medium for growth and energy.

An exemplary growth condition for achieving, one or more cannabinoid product(s) includes anaerobic culture or fermentation conditions. In certain embodiments, the microbial organism can be sustained, cultured or fermented under anaerobic or microaerobic conditions. Briefly, anaerobic conditions refer to an environment devoid of oxygen. Microaerobic conditions include, for example, a culture, batch fermentation or continuous fermentation such that the dissolved oxygen concentration in the medium remains above 0% saturation, such as between 0 and 10% of saturation. Microaerobic conditions also include growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions can be scaled up and grown continuously for manufacturing cannabinoid product. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of cannabinoid product. Fermentation procedures are well known in the art. Briefly, fermentation for the biosynthetic production of cannabinoid product can be utilized in, for example, fed-batch fermentation and batch separation; fed-batch fermentation and continuous separation, or continuous fermentation and continuous separation. Examples of batch and continuous fermentation procedures are well known in the art. Typically cells are grown at a temperature in the range of about 25° C. to about 40° C. in an appropriate medium, as well as up to 70° C. for thermophilic microorganisms.

The culture medium may include a feed molecule or molecules that is/are converted into a cannabinoid precursor, such as, but not limited to, $CO_2$, acetate, malonate, beta-alanine, aspartate, glutamate, oxaloacetate, hexanoate, butanoate, hexanol, butanol, prenol, isoprenol, or geraniol. The feed molecule can also serve as the main or a supplemental carbon source for cell growth and energy, or can be provided in addition to a sugar, sugar alcohol, polyol, or organic acid that is provided for growth and energy. Additional supplements can optionally include biotin, thiamine, pantothenate, and/or 4'-phosphopantotheine.

The culture medium at the start of fermentation may have a pH of about 5 to about 7. The pH may be less than 11, less than 10, less than 9, or less than 8. In other embodiments the pH may be at least 2, at least 3, at least 4, at least 5, at least 6, or at least 7. In other embodiments, the pH of the medium may be about 6 to about 9.5; 6 to about 9, about 6 to 8 or about 8 to 9.

Methods of the present disclosure for recovery, decarboxylation, and/or purification of a cannabinoid take advantage of certain physical and chemical properties of cannabinoids in combination with the properties of cell cultures (fermentation broths) in which the cannabinoids are generated. Cannabinoids, whether in solid or liquid form, are essentially insoluble in aqueous solutions, but orders-of-magnitude more soluble in various organic solvents. Cannabinoids are much less soluble in aqueous solutions than other small molecules typically found in fermentation broths. Fermentation broths consist mainly of water plus microbial cells, cellular fragments and macromolecules, nutrients required for microbe growth, impurities that may accompany the nutrients and metabolites—both intracellular and extracellular—that are byproducts of microbial metabolism. In addition, cannabinoids are smaller molecules than cellular materials that may be insoluble in water.

In aspects of the disclosure, the fermentation broth after a period of fermentation and production of one or more cannabinoids can be described with regards to the solids content in the broth. For example, exemplary amounts of total solids, as measured in percent weight (% wt.) in the broth can be in the range of about 1% (wt.) to about 50% (wt.), about 1% (wt.) to about 40% (wt.), 1% (wt.) to about 25% (wt.), 1% (wt.) to about 20% (wt.), 1% (wt.) to about 15% (wt.), 1% (wt.) to about 10% (wt.), or about 1% (wt.) to about 5% (wt.).

After a period of fermentation, total solids in the broth can include components such as protein, fat, fibers, ash, carbohydrates, steroids, antibiotics, vitamins, and ammonia/ammonium, in addition to one or more cannabinoids. Of the total solids in the broth the components can be in exemplary ranges as follows: 1% (wt.) to about 50% (wt.), about 1% (wt.) to about 40% (wt.), 1% (wt.) to about 25% (wt.), 1% (wt.) to about 20% (wt.), 1% (wt.) to about 15% (wt.), 1% (wt.) to about 10% (wt.), or about 1% (wt.) to about 5% (wt.) cannabinoid, about 15% to about 60% protein, about 1% to about 15% fat, about 1% to about 6% fibers, about 5% to about 35% ash, about 5% to about 27% carbohydrates.

Cannabinoids may be solids or liquids depending on the temperature. The melting point varies, depending on the identity of the cannabinoid compound. In the solid state, cannabinoids are denser (heavier) than water, whereas, in liquid state, cannabinoids are less dense (lighter) than water. The fermentation temperature of the fermentation broth is typically below the melting point of cannabinoids.

Applicants have found that these characteristics of cannabinoids may be exploited to recover and purify cannabinoids, generated in cell cultures, from the myriad biological components of the cell culture.

Certain desirable cannabinoids are decarboxylated forms of acidic cannabinoids generated in a cell culture. For example, and without limitation, CBGA may be decarboxylated to CBG, CBDA may be decarboxylated to CBD, THCA may be decarboxylated to THC, Δ8-THCA may be decarboxylated to Δ8-THC, THCVA may be decarboxylated to THCV, CBVA may be decarboxylated to CBV, CBNA may be decarboxylated to CBN, CBGVA may be decarboxylated to CBGV, CBDVA may be decarboxylated to CBDV, and CBCVA may be decarboxylated to CBCV. Some embodiments of the methods according to the present disclosure include steps of decarboxylating an acidic cannabinoid generated in a cell culture to produce a decarboxylated cannabinoid. In some embodiments, acidic cannabinoids can be decarboxylated when dissolved in a heated organic solvent. Decarboxylation may be carried out by heating the cannabinoid solution to a temperature of from 60° C. to 250° C. at a pressure in excess of the vapor pressure of the solvent at the temperature. In some embodiments, the decarboxylation temperature is at least 70° C., in some at least 80° C., in some at least 90° C., in some at least 100° C., in some at least 110° C., and in some at least 120° C. Example 3 below demonstrates the decarboxylation of CBGA to CBG in an ethanol/water solution.

In some embodiments, a water-miscible organic solvent is used for extraction of cannabinoids. For example, according to a method of the disclosure, a water-miscible solvent is added to a cell culture or water reduced pellet, and this forms a solvent extraction mixture. The water-miscible phase can then be separated from the cellular material, using a suitable technique(s) such as g-force separation or filtration. After separation, the cannabinoid can be recovered from the water-miscible phase.

Methods of the disclosure can include one or more steps of separation using normal gravity or "enhanced" gravity force (collectively referred to as "g-force" separation) to separate components in a composition. An example of normal gravity force separation is separation by settling, wherein a composition is allowed to settle under the normal forces of earth's gravity without application of external force. Separation by settling can occur for a defined period of time suitable to separate components in a composition, such as minutes, hours, or days.

Embodiments of the disclosure where enhanced gravity force is used to separate components of a composition generally involve application of external force that subjects components in a composition to forces greater than those of normal gravity. Examples of enhanced gravity force separation techniques and apparatus include centrifugation, hydrocyclone, and spiral concentrators.

In some embodiments, the water-miscible organic solvent is a monoalcohol. In some embodiments, the water-miscible organic solvent is a polyalcohol. In some embodiments, the water-miscible organic solvent is selected from acetaldehyde; acetic acid; acetone; acetonitrile; 1,2-butanediol; 1,3-butanediol; 1,4-butanediol; 1-butanol, 2-butoxyethanol; butyric acid; diethanolamine; diethylenetriamine; dimethylformamide; dimethoxyethane; dimethyl sulfoxide; 1,4-dioxane; ethanol; ethylamine; ethylene glycol; formic acid; furfuryl alcohol; glycerol; methanol; methyl diethanolamine; methyl isocyanide; n-methyl-2-pyrrolidone; 1-propanol; 1,3-propanediol; 1,5-pentanediol; 2-propanol; propanoic acid; propylene glycol; pyridine; tetrahydrofuran; triethylene glycol; any combinations thereof; and any subset thereof (and combinations of such a subset).

In some embodiments, a water-immiscible organic solvent is used for extraction of cannabinoids. For example, according to a method of the disclosure, a water-immiscible solvent is added to a cell culture or water reduced pellet, and this forms a water-immiscible phase and an aqueous phase in the culture. The water-immiscible phase can then be separated from the aqueous phase using a suitable technique(s) such as g-force separation. After separation, the cannabinoid can be recovered from the water-immiscible phase.

In some embodiments, a water-immiscible organic solvent is used for extraction of cannabinoids. In some embodiments, the water-immiscible organic solvent is a non-polar or polar hydrophobic organic solvent. In some embodiments, the water-immiscible organic solvent is aromatic, aliphatic, or halogenated aliphatic. In some embodiments, the water-immiscible organic solvent is selected from alcohols comprising more than 4 carbons. Other examples of suitable solvents may include petroleum ethers, esters, ethers, ketones, nitrated or chlorinated hydrocarbons, carbon tetrachloride, chloroform, cyclohexane, 1,2-dichloroethane, dichloromethane, diethyl ether, dimethyl formamide, ethyl acetate, butyl acetate, heptane, hexane, heptanone, d-limonene, methyl-tert-butyl ether, pentane, toluene, 2,2,4-trimethylpentane, petroleum streams such as kerosene, naphtha or distillate streams, either as virgin crude cuts or as finished refinery products. In some embodiments, the esters, ethers, ketones, nitrated or chlorinated hydrocarbons have a carbon chain length of C4-C14. In some embodiments, the esters, ethers, ketones, nitrated or chlorinated hydrocarbons can have unsaturation, or branched chains. In some embodiments, the water-immiscible organic solvent is a natural or synthetic oil such as, vegetables oil, animal fat, petroleum oil, and flower and fruit oils.

In some embodiments, the solvent used for extraction of cannabinoids is food grade solvent. In some embodiments, the solvent used for the cannabinoid extraction is Class 3 or Class 2 solvents from the Food and Drug Administration Guidance of June 2017 (www.fda.gov/media/71737/download).

In some embodiments, the Class 3 or Class 2 food grade solvents are water-immiscible solvents. Non-limiting examples of Class 3 or Class 2 food grade water-immiscible solvents that can be used for extraction of cannabinoids include: Anisole, Butylacetate, tert-Butylmethyl ether, Chlorobenzene, Chloroform, Cumene, Cyclohexane, 1,2-Dichloroethene, Dichloromethane, 1,2-Dimethoxyethane, 1,4-Dioxane, Ethylacetate, Ethylether, Ethylformate, Heptane, Hexane, Isobutyl acetate, Isopropylacetate, Methylacetate, 3-Methyl-1-butanol, Methylbutylketone, Methylcyclohexane, Methylethylketone, Methylisobutyl ketone, 2-Methyl-1-propanol, N-Methylpyrrolidone, Pentane, 1-Pentanol, Propylacetate, Tetralin, Toluene, 1,1,2-Trichloroethene, Triethylamine, Xylene, and d-limonene.

In some embodiments, the Class 3 or Class 2 food grade solvents are water-miscible solvents. Non-limiting examples of Class 3 or Class 2 food grade water-miscible solvents that can be used for extraction of cannabinoids include: Acetic acid, Acetone, Acetonitrile, N,N-Dimethylacetamide, N,N-Dimethylformamide, Dimethylsulfoxide, Ethanol, Ethyleneglycol, Formic acid, Formamide, Methanol, 2-Methoxyethanol, Nitromethane, 1-Propanol, 2-Propanol, Pyridine, Sulfolane.

In some embodiments, the Class 3 or Class 2 food grade solvents are partially water-miscible solvents. Non-limiting examples of Class 3 or Class 2 food grade partially water-miscible solvents that can be used for extraction of cannabinoids include: 1-Butanol, Butan-1-ol, 2-Butanol, Butan-2-ol.

Method 1

One embodiment of the methods according to the present disclosure (demonstrated, for example, in Example 1 below with reference to FIG. 1) does not require an organic (carbon-containing) solvent. In some embodiments, organic solvents are excluded. In some embodiments, addition of organic solvents is excluded.

In this embodiment, following cultivation, the broth temperature is increased above the melting point of the desired cannabinoid product. The temperature above the melting point of the cannabinoid is typically at least 65° C., and may be between 65° C. and 100° C., between 65° C. and 95° C., between 65° C. and 90° C., between 70° C. and 100° C., between 70° C. and 95° C., between 70° C. and 90° C., between 75° C. and 100° C., between 75° C. and 95° C., or between 75° C. and 90° C. In some embodiments of the methods described herein, the temperature above the melting point of the cannabinoid is greater than the melting point of the cannabinoid and also at least 30° C., in some embodiments at least 35° C., in some embodiments at least 40° C., in some embodiments at least 50° C., in some embodiments at least 60° C., in some embodiments at least 70° C., and in some embodiments at least 80° C. This method is especially effective when the product is extracellular, whether the product is secreted during cultivation or whether the product is extracellular as a result of heating the broth or as a result of physical or chemical method of lysing cells. In its liquid state, the cannabinoid forms a separate liquid phase that is lighter than the aqueous broth. The liquid cannabinoid is then separated from the broth by g-force separation, while maintaining the broth temperature at a temperature above the cannabinoid melting point, such that the cannabinoid is concentrated in the light phase. G-force separation is typically carried out for at least 5 minutes, and in some embodiments at least 10 minutes, at least 20 minutes, at least 30 minutes, at least 45 minutes, at least 60 minutes, at least 90 minutes, or at least 120 minutes; whether by batch or continuous g-force separation methods. The heavy phase, which is depleted in the desired product cannabinoid, is typically discarded. By this approach 80% or more of the cannabinoid product may be recovered in the light phase.

In some embodiments, the purity of the cannabinoid is increased by filtering, preferably ultrafiltering, the light phase to further remove cells, cell fragments, and macromolecules that may be present in the light phase. Ultrafiltration is accomplished by passing the fluid through a filtration membrane having a molecular weight cutoff of from about 5 kilodaltons to about 5,000 kilodaltons, about 10 kilodaltons to about 5,000 kilodaltons, about 15 kilodaltons to about 5,000 kilodaltons, about 20 kilodaltons to about 5,000 kilodaltons, about 25 kilodaltons to about 5,000 kilodaltons, about 30 kilodaltons to about 5,000 kilodaltons, about 50 kilodaltons to about 5,000 kilodaltons, about 5, 10, 15, 20, 25, 30, 50, 100, 1000, or about 5000 kilodaltons. Typically, light phase temperature is maintained at a temperature above the cannabinoid melting point during filtration. In some embodiments, the purity is further increased by washing the filtered light phase with water. Washing consists of mixing the light phase with an excess of pure water, maintaining the temperature at a point above the cannabinoid melting point, and centrifuging to recover the light phase which is reduced in impurities. In various embodiments, the washing step can be repeated as many times as necessary to increase the cannabinoid purity on a dry basis to the desired level. Alternately, one or more washing steps can be carried out below the cannabinoid melting point. In such washing steps, solid state cannabinoid is recovered in the heavy phase, and the light phase is discarded. In some embodiments, one or more washing steps can be conducted above the cannabinoid melting point and one or more washing steps can be conducted below the cannabinoid melting point. If a dry final product is desired, the purified cannabinoid, whether in solid or liquid form, can be dried by any suitable conventional method or optionally lyophilized.

Optionally, temperature and pressure during any heated step are raised to levels sufficient to decarboxylate the cannabinoid, which is typically a temperature of from 60° C. to 250° C. at a pressure in excess of the vapor pressure of the solvent at the temperature. In some embodiments, the decarboxylation temperature is from 70° C. to 250° C., from 80° C. to 250° C., from 90° C. to 250° C., from 100° C. to 250° C., from 60° C. to 200° C., from 70° C. to 200° C., from 80° C. to 200° C., from 90° C. to 200° C., or from 100° C. to 200° C.

Method 2

Figure 2:
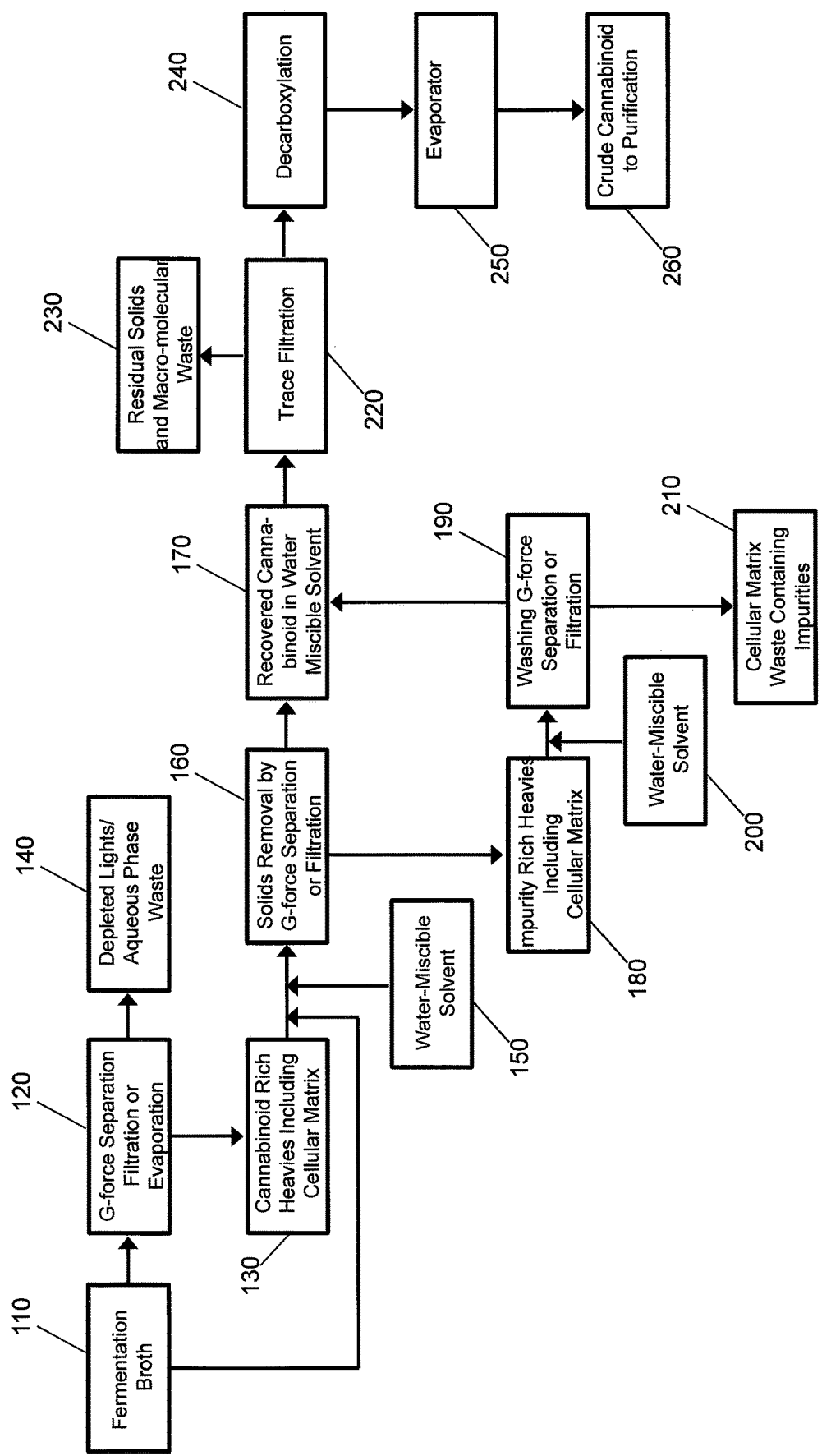
FIG. 2 is a flow chart for a process of recovery and purification of a cannabinoid from an engineered cell culture, as described in Example 2 herein.

Another embodiment of the methods according to the present disclosure (demonstrated, for example, in Example 2 below with reference to FIG. 2) employs a water-miscible organic (carbon-containing) solvent. Any suitable water-miscible organic solvent may be used. In some embodiments, the water-miscible organic solvent is a monoalcohol. In some embodiments, the water-miscible organic solvent is a polyalcohol. In some embodiments, the water-miscible organic solvent is selected from acetaldehyde; acetic acid; acetone; acetonitrile; 1,2-butanediol; 1,3-butanediol; 1,4-butanediol; 2-butoxyethanol; butyric acid; diethanolamine; diethylenetriamine; dimethylformamide; dimethoxyethane; dimethyl sulfoxide; 1,4-dioxane; ethanol; ethylamine; ethylene glycol; formic acid; furfuryl alcohol; glycerol; methanol; methyl diethanolamine; methyl isocyanide; n-methyl-2-pyrrolidone; 1-propanol; 1,3-propanediol; 1,5-pentanediol; 2-propanol; propanoic acid; propylene glycol;

pyridine; tetrahydrofuran; triethylene glycol; any combinations thereof; and any subset thereof (and combinations of such a subset). In some embodiments, the water-miscible organic solvent is ethanol. Ethanol is low-cost, easily recovered and reused, relatively safe, and in wide-spread use in food and pharmaceutical processing. Ethanol is also effective in permeabilizing microbial cell membranes to release intracellular and/or cell-associated cannabinoids.

In this embodiment, following cultivation, the broth temperature is set to a value below the melting point of the desired cannabinoid product and the broth is separated by centrifugation, evaporated, flocculated, or filtrated. G-force separation and filtration are the preferred methods. G-force separation or filtration is typically carried out for at least 5 minutes, and in some embodiments at least 10 minutes, at least 20 minutes, at least 30 minutes, at least 45 minutes, at least 60 minutes, at least 90 minutes, or at least 120 minutes; whether by batch or continuous g-force separation tor filtration methods. The heavy phase is concentrated in solids including the cannabinoid product and the cellular material. The light phase, which is depleted in the product, is typically discarded. By this approach 80% or more the cannabinoid product is recovered in the heavy phase.

The water-miscible organic solvent (typically ethanol) is then added to the heavy phase or cell culture medium directly in sufficient quantity to dissolve (solubilize) the cannabinoid. In some embodiments of this method the weight ratio of water-miscible organic solvent to water in the first heavy phase is between 15/85 and 85/15, between 40/60 and 85/15, between 50/50 and 80/20, or between 55/45 and 75/25, after addition of the water-miscible organic solvent. If some cases, additional water may be added to that already present, to achieve the desired weight ratio of water-miscible organic solvent to water.

This is followed by a second g-force separation or filtration to remove insoluble cellular material in the resulting heavy phase. The second g-force separation or filtration is typically carried out for at least 5 minutes, and in some embodiments at least 10 minutes, at least 20 minutes, at least 30 minutes, at least 45 minutes, at least 60 minutes, at least 90 minutes, or at least 120 minutes; whether by batch or continuous g-force separation or filtration methods. The resulting cannabinoid rich light phase is substantially free of insoluble cellular material. It may be desirable to wash the heavy phase one or more times by adding additional water-miscible organic solvent and centrifuging-force separating or filtrating, to reduce the loss of cannabinoid in the heavy phase before it is discarded. Resulting light phases are combined. The purity of the cannabinoid in the combined light phase from the solids removal step and the washing steps may be increased by filtration, preferably ultrafiltration, to remove cells, cell fragments, and macromolecules that may be present. Ultrafiltration is accomplished by passing the fluid through a filtration membrane having a molecular weight cutoff of from about 5 kilodaltons to about 5,000 kilodaltons, about 10 kilodaltons to about 5,000 kilodaltons, about 15 kilodaltons to about 5,000 kilodaltons, about 20 kilodaltons to about 5,000 kilodaltons, about 25 kilodaltons to about 5,000 kilodaltons, about 30 kilodaltons to about 5,000 kilodaltons, about 50 kilodaltons to about 5,000 kilodaltons, about 5, 10, 15, 20, 25, 30, 50, 100, 1000, or about 5000 kilodaltons.

The water-miscible organic solvent may then be removed from the light phase by any suitable means, which may include heating, optionally under vacuum, to evaporate the water-miscible organic solvent. With the depletion of water-miscible organic solvent, the cannabinoid precipitates in the remaining aqueous solution. The vapor of the water-miscible organic solvent may be captured and condensed for recycle. The aqueous solution containing the cannabinoid is then centrifuged to concentrate the cannabinoid in the heavy phase. It may be desirable to wash the heavy phase one or more times by adding an excess of water and centrifuging to increase the cannabinoid purity on a dry basis. If a dry final product is desired, the purified cannabinoid, whether in solid or liquid form, can be dried by any suitable conventional method or optionally lyophilized.

Optionally, temperature and pressure during removal of the water-miscible organic solvent may be raised to levels sufficient to decarboxylate the cannabinoid, which is typically a temperature of from 60° C. to 250° C. at a pressure in excess of the vapor pressure of the solvent at the temperature. In some embodiments, the decarboxylation temperature is from 70° C. to 250° C., from 80° C. to 250° C., from 90° C. to 250° C., from 100° C. to 250° C., from 60° C. to 200° C., from 70° C. to 200° C., from 80° C. to 200° C., from 90° C. to 200° C., or from 100° C. to 200° C.

In some embodiments of the methods described herein, temperatures below the melting point of the cannabinoid are less than the melting point of the cannabinoid and also no more than 10° C., in some embodiments no more than 15° C., in some embodiments no more than 20° C., in some embodiments no more than 25° C., in some embodiments no more than 30° C., in some embodiments no more than 35° C., in some embodiments no more than 40° C., and in some embodiments no more than 45° C.

Method 3

A further embodiment of the methods according to the present disclosure employs a water-immiscible organic (carbon-containing) solvent. Any suitable water-immiscible organic solvent may be used. In some embodiments, the water-immiscible organic solvent is a non-polar or polar hydrophobic organic solvent. In some embodiments, the water-immiscible organic solvent is aromatic, aliphatic, or halogenated aliphatic. In some embodiments, the water-immiscible organic solvent is selected from alcohols comprising more than 4 carbons. Other examples of suitable solvents may include petroleum ethers, esters, ethers, ketones, nitrated or chlorinated hydrocarbons, carbon tetrachloride, chloroform, cyclohexane, 1,2-dichloroethane, dichloromethane, diethyl ether, d-limonene, ethyl acetate, heptane, hexane, methyl-tert-butyl ether, pentane, toluene, 2,2,4-trimethylpentane, petroleum streams such as kerosene, naphtha or distillate streams, either as virgin crude cuts or as finished refinery products. In some embodiments, the water-immiscible organic solvent is a natural or synthetic oil such as vegetables oil, animal fat, petroleum oil, or flower and fruit oils.

In this embodiment, and with reference to FIG. 4A, following cultivation, the broth temperature is set to a value below the melting point of the desired cannabinoid product and the broth is separated using g-force, evaporated, flocculated or filtered 320. G-force separation and filtration are the preferred methods. G-force separation or filtration is typically carried out for at least 5 minutes, and in some embodiments at least 10 minutes, at least 20 minutes, at least 30 minutes, at least 45 minutes, at least 60 minutes, at least 90 minutes, or at least 120 minutes; whether by batch or continuous g-force separation or filtration methods. The heavy phase 330 is concentrated in solids including the cannabinoid product and the cellular material. The light phase 325, which is depleted in the product, is typically discarded. By this approach 80% or more the cannabinoid product is recovered in the heavy phase.

In some embodiments of the methods described herein, the broth temperature is set below the melting point of the cannabinoid and is also no more than 10° C. less than the melting point of the cannabinoid, in some embodiments no more than 15° C., in some embodiments no more than 20° C., in some embodiments no more than 25° C., in some embodiments no more than 30° C., in some embodiments no more than 35° C., in some embodiments no more than 40° C., and in some embodiments no more than 45° C. less than the melting point of the cannabinoid.

The water-immiscible organic solvent is then added to the g-force separated or filtered heavy phase or directly to the cell culture medium in sufficient quantity to dissolve (solubilize) the cannabinoid. This is followed by a subsequent g-force separation to remove insoluble cellular material in the resulting cannabinoid-containing solvent phase, which can either be a light phase or a heavy phase depending on solvent properties. The subsequent g-force separation is typically carried out for at least 5 minutes, and in some embodiments at least 10 minutes, at least 20 minutes, at least 30 minutes, at least 45 minutes, at least 60 minutes, at least 90 minutes, or at least 120 minutes; whether by batch or continuous g-force separation methods. Optionally, the subsequent separation is carried out at a temperature above the cannabinoid melting point, as described above in relation to methods 1 and 2. The resulting cannabinoid rich solvent phase is substantially free of insoluble cellular material. It may be desirable to wash the solvent phase one or more times by adding additional water-immiscible organic solvent to the heavy phase and g-force separating (optionally at a temperature above the cannabinoid melting point) the solvent mixture, to reduce the loss of cannabinoid in the solvent phase before it is discarded. Resulting solvent phases are combined. The purity of the cannabinoid in the combined solvent phase from the solids removal step and the washing steps may be increased by filtration, preferably ultrafiltration, to remove cellular material (which may include cells, cell fragments, and macromolecules) that may be present. Ultrafiltration is accomplished by passing the fluid through a filtration membrane having a molecular weight cutoff of from about 5 kilodaltons to about 5,000 kilodaltons, about 10 kilodaltons to about 5,000 kilodaltons, about 15 kilodaltons to about 5,000 kilodaltons, about 20 kilodaltons to about 5,000 kilodaltons, about 25 kilodaltons to about 5,000 kilodaltons, about 30 kilodaltons to about 5,000 kilodaltons, about 50 kilodaltons to about 5,000 kilodaltons, about 5, 10, 15, 20, 25, 30, 50, 100, 1000, or about 5000 kilodaltons, optionally at a temperature above the cannabinoid melting point.

The water-immiscible organic solvent may then be removed from the light phase by any suitable means, which may include heating, optionally under vacuum, to evaporate the water-immiscible organic solvent. Optionally, temperature and pressure during removal of the water-immiscible organic solvent or during any heated step of this process may be raised to levels sufficient to decarboxylate the cannabinoid, which is typically a temperature of from 60° C. to 250° C. at a pressure in excess of the vapor pressure of the solvent at the temperature. In some embodiments, the decarboxylation temperature is from 70° C. to 250° C., from 80° C. to 250° C., from 90° C. to 250° C., from 100° C. to 250° C., from 60° C. to 200° C., from 70° C. to 200° C., from 80° C. to 200° C., from 90° C. to 200° C., or from 100° C. to 200° C.

Steps described above as parts of Methods 1, 2, and 3 may be combined in any suitable order to provide hybrid methods of recovery, decarboxylation, and/or purification of a cannabinoid.

Method 4

Figure 4A:
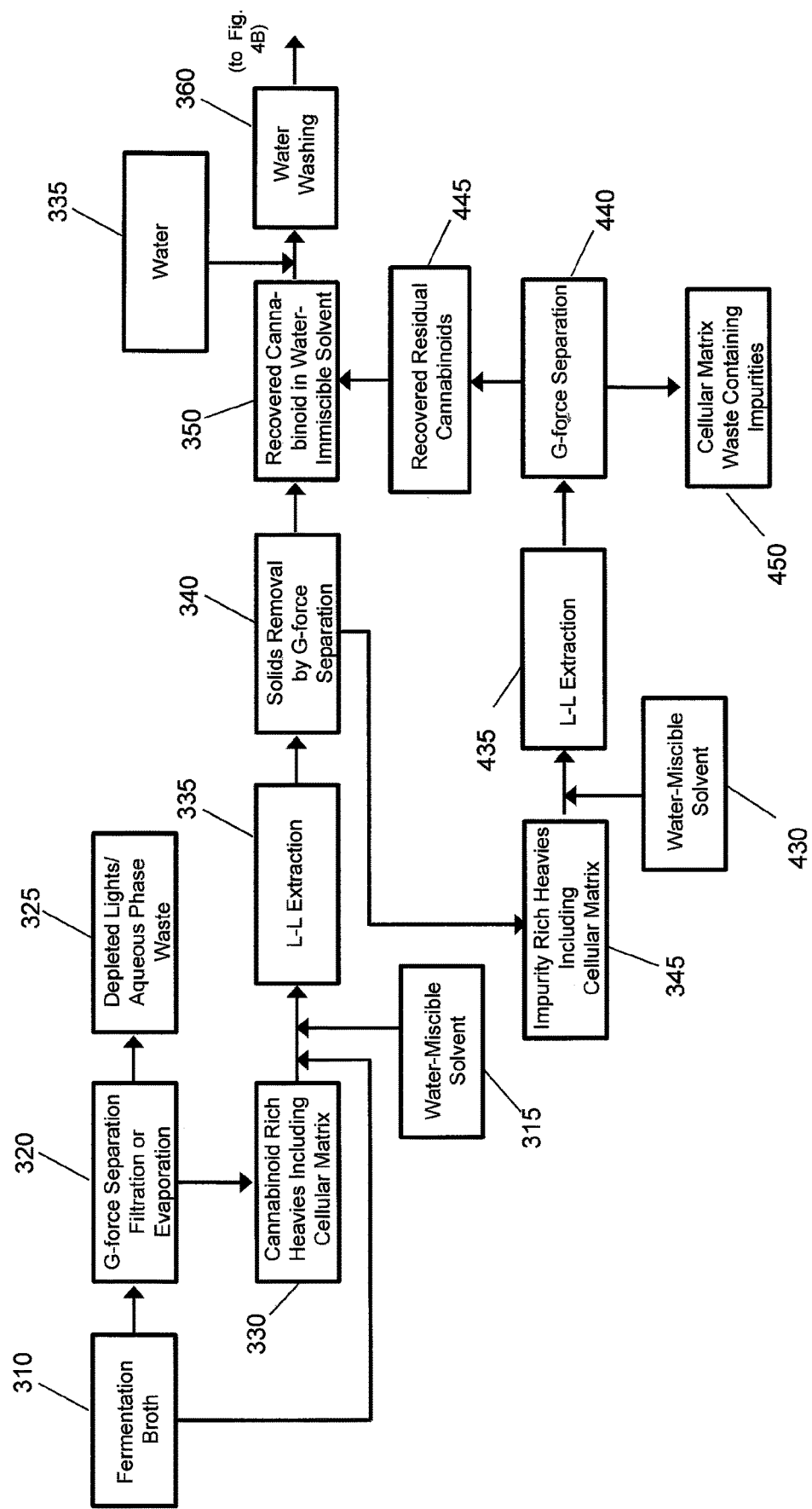
FIGS. 4A and 4B show an exemplary flow diagram of liquid-liquid extraction of cannabinoid.
Figure 4B:
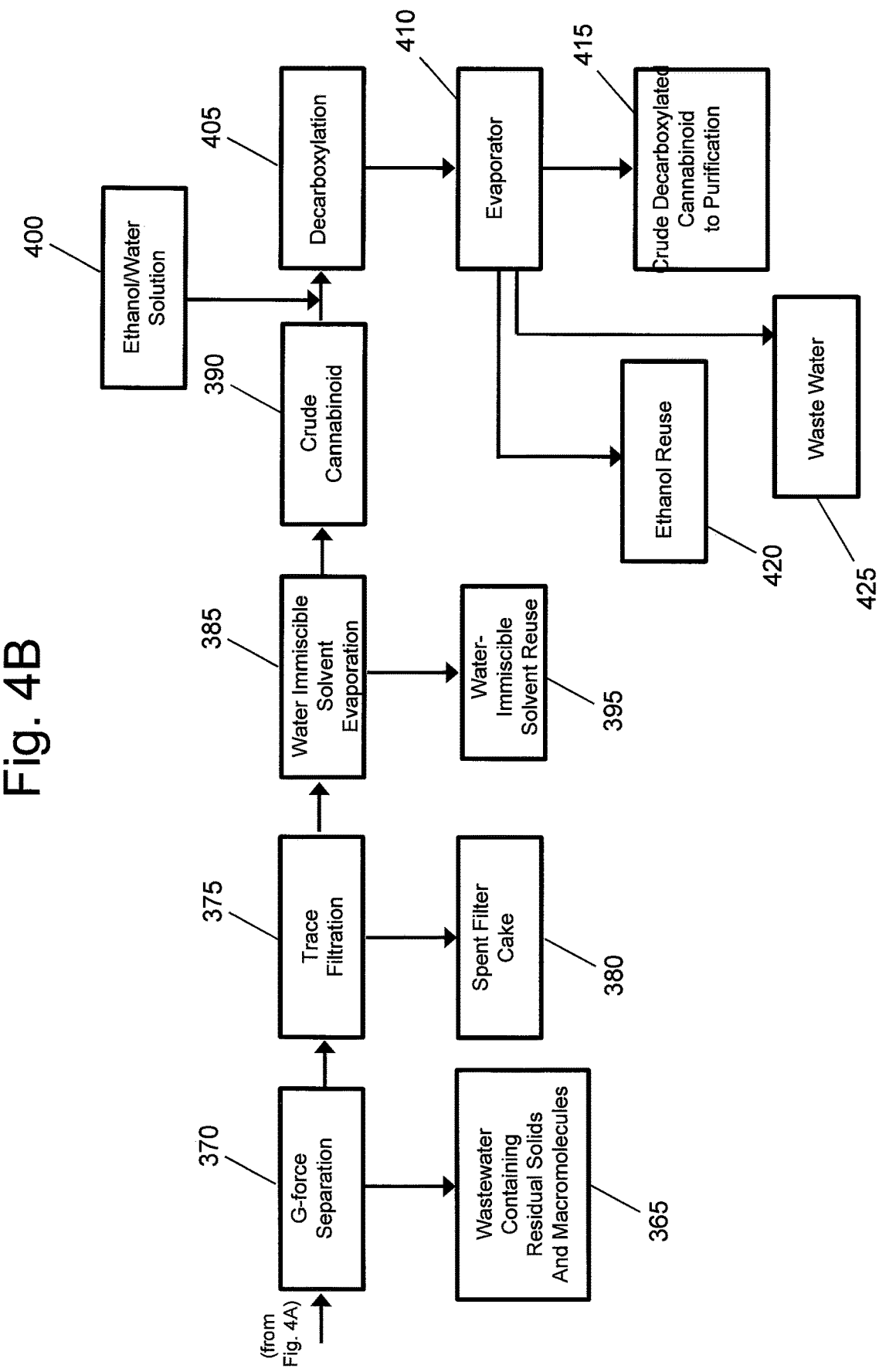

FIGS. 4A and 4B show an exemplary flow diagram of liquid-liquid extraction of cannabinoid using Method 4. In the method, a cell culture comprising cells engineered to produce a cannabinoid in a culture medium in a fermenter 310. A water-immiscible solvent 315 is added to the culture medium in vessel 335 and mixed for liquid-liquid extraction (L-L extraction). This in turn forms a water-immiscible phase which includes cannabinoid, and an aqueous phase. Next, a separation vessel or device 340 is used to separate the water-immiscible phase from the aqueous phase, such as by gravity settling or/and centrifugation, resulting in the water-immiscible phase capturing the cannabinoid 350. A biosolid 345 (e.g., cell pellet) can be generated as a result of the separation. Water-immiscible solvent 430 is added to the biosolid 345 for secondary recovery of the cannabinoid from the biosolid in L-L extractor 435. The extraction mixer is G-force separated 440 to recover the residual cannabinoid 445 and to remove cellular matrix waste containing impurities 450. The residual cannabinoid 445 is combined in the recovered cannabinoid 350. Next, water 355 can be added to wash the vessel 360 to remove impurities from the cannabinoid-containing water-immiscible phase. Next, moving from FIG. 4A to 4B and as part of the overall process, another or the same separation vessel or device 370 is used to separate the water-immiscible phase from the wash water. Wastewater 365 can be generated as a result of the wash. Residual solids and macromolecules 380 can be removed in the filtration unit 375. The water-immiscible solvent can be removed in evaporation vessel 385 to produce crude cannabinoid 390 and to generate a water-immiscible solvent stream 395. Ethanol/water 400 solution can be added to the crude cannabinoid 390. Next, the cannabinoid can be subjected to decarboxylation 405 in the same ethanol solution phase. Alternatively, the crude cannabinoid in the water immiscible phase can be directly decarboxylated in the decarboxylation vessel 405. After the cannabinoid is decarboxylated either in the original water immiscible extraction solvent, or ethanol/water solution, the composition is subject to solvent evaporation in evaporation device 410. Crude product 415 can be generated ethanol 420 can be recovered for reuse and wastewater 425 is discarded. The crude cannabinoid produced 415 can optionally be processed in one or more processing or purification steps (not shown). Exemplary embodiments of the process are described in more detail herein.

Any suitable water-immiscible organic solvent may be used. In some embodiments, the water-immiscible organic solvent is a non-polar or polar hydrophobic organic solvent. In some embodiments, the water-immiscible organic solvent is aromatic, aliphatic, or halogenated aliphatic. In some embodiments, the water-immiscible organic solvent is selected from alcohols comprising more than 4 carbons. Other examples of suitable solvents may include petroleum ethers, esters, ethers, ketones, nitrated or chlorinated hydrocarbons, carbon tetrachloride, chloroform, cyclohexane, 1,2-dichloroethane, dichloromethane, diethyl ether, ethyl acetate, butyl acetate, heptane, hexane, heptanone, methyl-tert-butyl ether, pentane, toluene, 2,2,4-trimethylpentane, d-limonene, petroleum streams such as kerosene, naphtha or distillate streams, either as virgin crude cuts or as finished refinery products. In some embodiments, the esters, ethers, ketones, nitrated or chlorinated hydrocarbons have a carbon chain length of C4-C14. In some embodiments, the esters, ethers, ketones, nitrated or chlorinated hydrocarbons can have unsaturation, or branched chains. In some embodiments, the water-immiscible organic solvent is a natural or synthetic oil such as vegetables oil, animal fat, petroleum oil, or flower and fruit oils.

In this embodiment and with reference to the process described in FIGS. 4A and 4B, following cultivation (310), the culture medium temperature is set to between 20 to 120° C., preferably between 20 to 50° C. The selected water-immiscible organic solvent 315 is mixed with the culture medium at desired ratio, such as a culture medium:solvent weight ratio in the range of 0.1:1 to 10:1 respectively; and preferably at a weight ratio in the range of 5:1 to 10:1 (culture medium:solvent). The mixing can be conducted in any suitable way, including directly mixing inside fermenter; using an inline mixer; or an intermediate stirred tank; or combination of different mixing methods (335).

The pH of the culture medium can be in any range from 2 to 9 and adjusted by any kind of acids as needed; preferably, the culture medium pH is the in range of 5 to 7. Contact (mixing) time of culture medium and the water-immiscible solvent can be 10 min to 10 hours; preferably, between 30 min to 3 hours. The mixture of culture medium and the water-immiscible solvent is then separated into two phases either by g-force separation (340). The phase of water-immiscible solvent containing cannabinoid products is retained; the aqueous phase containing the microbial cells (345) is discarded after heat or chemical kill. By this approach 80% or more of the cannabinoid product is recovered in the water-immiscible phase 350.

Resulting organic solvent phase(s) is water washed multiple times in water washing vessel 360 by adding water 355 and separated by g-force separation (370). The aqueous phase is discarded as waste stream (365). The organic solvent phase is optionally pass through a filtration step 375 to remove residual cells, cell fragments, macromolecules, and suspended solids 380 that may be present. The filtration unit is preferably an ultrafiltration with filtration membrane having a molecular weight cutoff of from about 5 kilodaltons to about 5,000 kilodaltons, about 10 kilodaltons to about 5,000 kilodaltons, about 15 kilodaltons to about 5,000 kilodaltons, about 20 kilodaltons to about 5,000 kilodaltons, about 25 kilodaltons to about 5,000 kilodaltons, about 30 kilodaltons to about 5,000 kilodaltons, about 50 kilodaltons to about 5,000 kilodaltons, about 5, 10, 15, 20, 25, 30, 50, 100, 1000, or about 5000 kilodaltons.

The water-immiscible organic solvent may then be removed by any suitable means, which may include heating, optionally under vacuum, to evaporate 385 the water-immiscible organic solvent for reuse 395 and produce crude cannabinoid 390. Optionally, temperature and pressure during removal of the water-immiscible organic solvent or during any heated step of this process may be raised to levels sufficient to decarboxylate the cannabinoid 405, which is typically a temperature of from 60° C. to 250° C. at a pressure in excess of the vapor pressure of the solvent at the temperature. In some embodiments, the decarboxylation temperature is from 70° C. to 250° C., from 80° C. to 250° C., from 90° C. to 250° C., from 100° C. to 250° C., from 60° C. to 200° C., from 70° C. to 200° C., from 80° C. to 200° C., from 90° C. to 200° C., or from 100° C. to 200° C.

Optionally, the water-immiscible solvent is completely removed at suitable temperature and pressure that minimize the decarboxylation and a crude cannabinoid acid product (CBGA) is obtained. Preferably, temperature for the solvent removal is in the range of 10 to 110° C.; pressure of 0.01 bar to 1 bar.

Optionally, decarboxylation of crude cannabinoid acid 390 can be conducted in the same water-immiscible solvent from the trace filtration unit (375), or in a different solvent (400) by re-dissolving the crude cannabinoid acid 390 that is obtained from the water-immiscible solvent evaporation. The different solvent can be water-immiscible, or water-miscible, including but not limited to C1-C4 alcohols; polyols such as ethylene glycol, propylene glycol, butane-diols; dimethyl sulfoxide (DMSO).

Method 5

Operation conditions and procedure is set similar to those described in Method 2 omitting the first g-force separation or filtration step.

Method 6

A further embodiment of the methods according to the present disclosure involves contacting a surface of a fermentation vessel with an alkaline solution to recover cannabinoid from the surface after a fermentation process. The alkaline solution washing process can be performed after any cannabinoid fermentation process, including those described herein, to increase overall recovery of the cannabinoid. Cannabinoid recovered using the washing process can be combined with cannabinoid obtained using any method of the disclosure.

In the method, cell culture comprising cells engineered to produce a cannabinoid in a culture medium and cannabinoid is removed from a fermentation vessel. The fermentation vessel typically will have inner surfaces with at least a portion of the inner surfaces having been in contact with the cannabinoid. During the fermentation, process, a portion of the cannabinoid becomes associated with the inner surfaces of the fermentation vessel and remains associated when the broth is removed.

After the fermentation broth is removed, an amount of an alkaline liquid composition is added to the fermentation vessel to recover cannabinoid from the inner surfaces. In some embodiments, a volume of alkaline liquid is added that is a small fraction of the volume of fermentation broth removed so that cannabinoid removed from the vessel is not too dilute in the liquid phase. The cannabinoid can be dissolved or suspended in the liquid phase depending on the amount of caustic solution added. Any suitable technique(s), such as agitation, spraying, etc., can be used to ensure the alkaline solution is in contact with the surface of the vessel for removal of the cannabinoid. Optionally, the alkaline solution can contact the surface at an elevated temperature, such as about 25° C. or greater, one or more temperatures in the range of about 25° C. to about 100° C., or even greater than 100° C.

The alkaline solution can include one of more alkali metal hydroxide (such as NaOH and/or KOH), or alkaline earth metal hydroxide. The concentration of the hydroxide(s) can be about 0.1N or greater, such as in the range of about 0.1N to about 3N or greater.

In some aspects the alkaline solution can be analyzed to obtain information on the removal of cannabinoid from the vessel surface.

After removal of the cannabinoid, a step of neutralizing can be performed by adding an acid such as an inorganic or organic acid, like hydrochloric acid, sulfuric acid, acetic acid, and/or nitric acid, to the alkaline solution comprising the cannabinoid, so the solution becomes pH neutral.

The method can also further include a step of contacting the acid-neutralized solution with a water immiscible solvent, such as butyl acetate, in order to extract the cannabinoid from the solution to the solvent. Alternatively, the solution can be filtered and the retentate can be dissolved in a solvent. The water immiscible solvent with cannabinoid can then be combined with cannabinoid obtained from the fermentation medium.

EXAMPLES

Unless otherwise noted, all reagents were obtained or are available from Aldrich Chemical Co., Milwaukee, Wisconsin, or may be synthesized by known methods.

Example 1: Recovery and Purification of a Cannabinoid from an Engineered Cell Culture by First Method With reference to FIG. 1, cell culture (fermentation broth) 10 comprising cells engineered to produce a cannabinoid in a culture medium and a cannabinoid so produced is harvested and heated (20) to a temperature T above the melting point MP of the cannabinoid and deposited in heated g-force separator 30. Cell culture (fermentation broth) 10 is g-force separated to separate cannabinoid-rich light phase 40 comprising liquid-phase cannabinoid, from cannabinoid-depleted heavy phase 50, comprising culture medium, cells, and insoluble and aqueous-soluble cellular components. During g-force separation, temperature T of cell culture (fermentation broth) 10 is maintained above melting point MP of the cannabinoid. Cannabinoid-depleted heavy phase 40 is discarded. Cannabinoid-rich light phase 40 is recovered and water is added 60, then passed through g-force separation unit 70. Residual solids and macromolecules 80 separated from cannabinoid-rich light phase 90. During g-force separation (20 and 50), temperature T is maintained above melting point MP of the cannabinoid. Cannabinoid-depleted impurity rich cellular matrix waste 50 is discarded. Higher purity cannabinoid-rich light phase 90 is produced through waster washing g-force separation 70.

Optionally, temperature and pressure during any heated step are raised to levels sufficient to decarboxylate the cannabinoid, which is typically a temperature of from 60° C. to 250° C. at a pressure in excess of the vapor pressure of the solvent at the temperature.

Example 2: Recovery and Purification of a Cannabinoid from an Engineered Cell Culture by Second Method With reference to FIG. 2, cell culture (fermentation broth) 110 comprising cells engineered to produce a cannabinoid in a culture medium and a cannabinoid so produced is maintained at a temperature T below the melting point MP of the cannabinoid and deposited in a g-force separator, evaporator, flocculation or filtration unit 120. G-force separator and filtration are preferred methods. Cell culture (fermentation broth) 110 is separated under g-force or filtered into cannabinoid-depleted light phase 140, which is the supernatant comprising culture medium, from cannabinoid-rich heavy phase 130, which is in the form of a pellet comprising cells, insoluble cellular components, and the desired cannabinoid. During g-force separation or filtration, temperature T of cell culture (fermentation broth) 110 is maintained below melting point MP of the cannabinoid. Cannabinoid-depleted light phase 140 is discarded. Ethanol is used as a water miscible solvent 150, which is added to cannabinoid-rich heavy phase 130, and the solution is processed through the g-force separator or filtration unit 160. G-force separation or filtration separates high purity cannabinoid light phase 170 comprising the cannabinoid, from cannabinoid-depleted heavy phase 180, comprising cells, and insoluble and aqueous-soluble cellular components. During this subsequent g-force separation or filtration, temperature T of is maintained below melting point MP of the cannabinoid. Optionally, cannabinoid-depleted heavy phase 180 is subject to a subsequent g-force separation or filtration in washing g-force separator or filtration unit 190 after addition of additional water-miscible solvent 200 like ethanol, at a temperature T below the melting point MP of the cannabinoid, after which impurities—rich heavy phase 210 is discarded and high purity cannabinoid light phase is combined with separates high purity cannabinoid light phase 170. The combined high purity cannabinoid light phase 70 is passed through filter 220, which is an ultrafilter having a molecular weight cutoff of from about 5 kilodaltons to about 5,000 kilodaltons, about 10 kilodaltons to about 5,000 kilodaltons, about 15 kilodaltons to about 5,000 kilodaltons, about 20 kilodaltons to about 5,000 kilodaltons, about 25 kilodaltons to about 5,000 kilodaltons, about 30 kilodaltons to about 5,000 kilodaltons, about 50 kilodaltons to about 5,000 kilodaltons, about 5, 10, 15, 20, 25, 30, 50, 100, 1000, or about 5000 kilodaltons. During ultrafiltration, temperature T of combined high purity cannabinoid light phase 170 is maintained below melting point MP of the cannabinoid. Residual solids and macromolecules 230 separated from combined high purity cannabinoid light phase 170, by filter 220 are discarded. After filtration, filtered light phase is decarboxylated in decarboxylation unit 240. The ethanol/water solution from decarboxylation unit is evaporated in evaporator 250 and decarboxylated crude cannabinoid 260 is produced.

Example 3: Decarboxylation of CBGA to CBG in Ethanol/Water Solution

Figure 3:
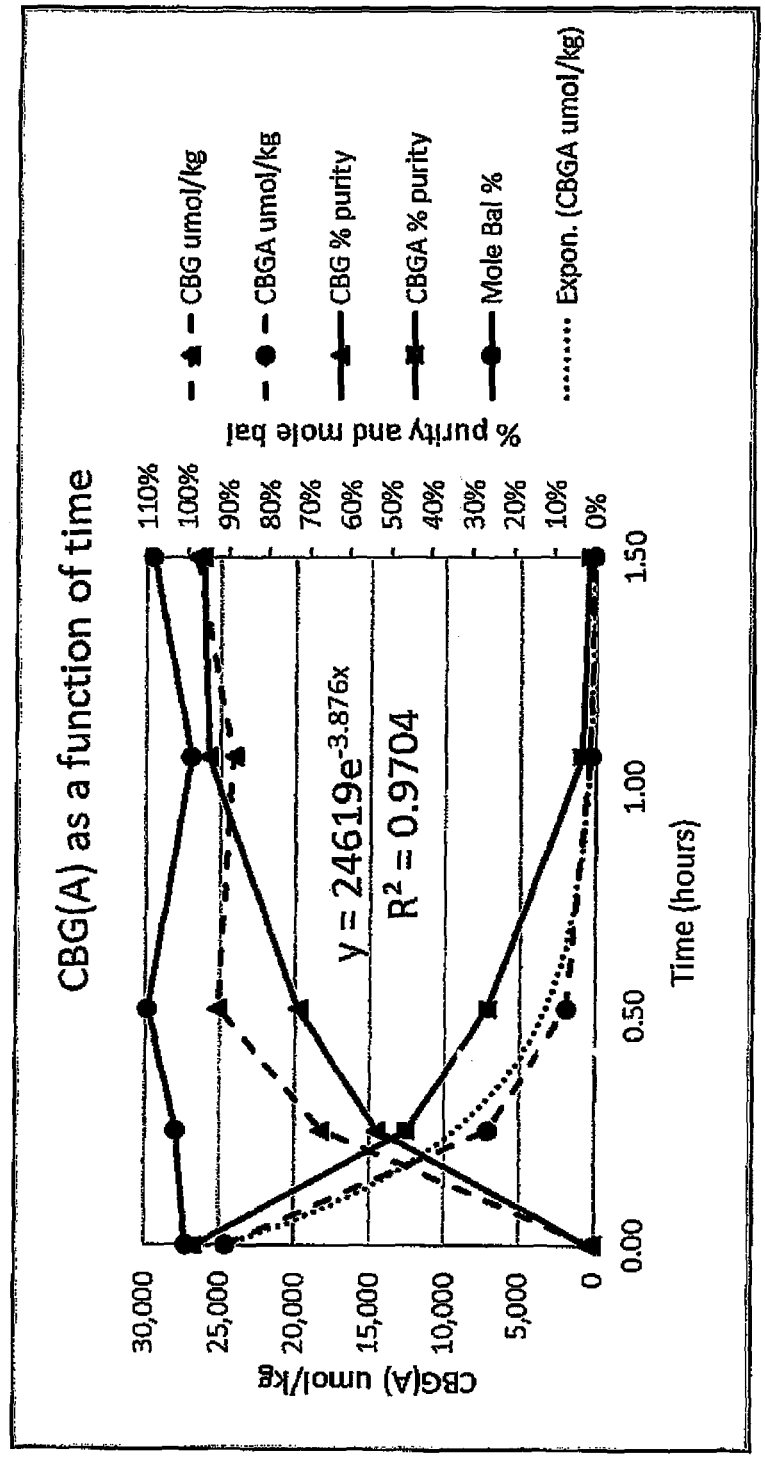
FIG. 3 is a graph of CBG and CBGA concentration as a function of time during decarboxylation, as described in Example 3.

A CBGA stock solution was prepared by dissolving CBGA in 1.56 g of 66 w/w % ethanol to obtain a final CBGA concentration of 1.01 w/w %. 0.2 mL of stock solution was aliquoted into four pressure-rated glass tubes, purged with nitrogen, and sealed. The tubes were placed in a pre-heated oven at 110° C. for 15, 31, 64, and 90 minutes. The resulting liquid was analyzed by HPLC for CBGA and CBG concentration. The first order rate constant was calculated to be 3.88 $hr^{-1}$. The 90-minute sample resulted in 108% CBG yield. An unknown impurity in the CBGA stock solution likely reacted to CBG resulting in >100% yield. CBG purity was measured by HPLC. In the 90-min sample, purity of the CBG was 96.4%, on a dry-basis. FIG. 3 is a graph of CBG and CBGA concentration as a function of time during decarboxylation.

TABLE 1

HPLC dry-basis purity of CBG and CBGA as a function of time

| | HPLC Rel. Area % | | | |
| --- | --- | --- | --- | --- |
| Time (min) | Unknown | CBGA | CBG | Other |
| 0 | 7.21 | 90.95 | 1.21 | 0.63 |
| 15 | 4.21 | 44 | 51.14 | 0.65 |
| 31 | 2.26 | 25.63 | 71.03 | 1.08 |
| 64 | 0.03 | 3.42 | 94.71 | 1.84 |
| 90 | 0 | 1.57 | 96.41 | 2.02 |

Various modifications and alterations of this disclosure will become apparent to those skilled in the art without departing from the scope and principles of this disclosure, and it should be understood that this disclosure is not to be unduly limited to the illustrative embodiments set forth hereinabove.

Example 4: Recovery and Purification of a Cannabinoid from an Engineered Cell Culture by Method 4

500 g of the cell culture (broth) comprising cells engineered to produce one or more cannabinoids in a culture medium was mixed with 100 g butyl acetate at 25° C. Broth pH is 6.8 after fermentation and was used without further adjustment. The mixture was mixed vigorously in a sealed beaker with magnetic stir bar for 1.5 hours. The mixture was then centrifuged with a bucket centrifuge at 8000 g-force and for 5 min. The top supernatant was siphoned out manually. Samples from both light and heavy phase were analyzed by HPLC for CBGA/CBG concentration. CBGA/CBG in butyl acetate phase was 98% of that in the original culture medium.

Example 5: Extraction of Cannabinoids Using Various Solvents

The semi-solid that was obtained from centrifugation of the culture medium and that consisted of cell mass and CBGA was re-suspended in DI-water at a water to semi-solid ratio of 4 to 1 by weight. 20% by weight of a selected solvent as shown in Table 2 was then added to the re-suspended solution and mixed by stirring at the room temperature (~20° C.) for 90 min. The mixture was then centrifuged at 8000 g-force for 5 min to separate the mixture into two phases. Sample of organic solvent layer was taken for HPLC analysis for CBGA/CBG concentration; recovery was calculated by assuming a perfect phase separation and solvent loss to aqueous phase was neglected. The percent recoveries of CBGA and CBG produced in the total cell culture broth using various solvents are shown in Table 2 below.

TABLE 2

| Solvent | CBGA + CBG % Recovery |
| --- | --- |
| Butyl Acetate | 69% |
| Ethyl Acetate | 100% |
| Hexane | 60% |
| Chloroform | 67% |
| Heptanone | 68% |

Additionally, the percent recovery of CBGA and CBG produced in the total cell culture medium using ethanol and butyl acetate were also compared. Briefly, for ethanol extraction, the culture medium was first centrifuged at 8000 g-force for 3 min and the supernatants were decanted. Some cannabinoid may remain in the supernatant. Following centrifugation, the cannabinoid product may remain in a mix with cells and form the precipitate, i.e, the heavy phase. Two times by weight of pure ethanol was then added to the heavy phase and was stirred to re-disperse and continue to stir for 10 min. The mixture was then subject to centrifuge again, the supernatant was collected and analyzed. CBGA recovery was shown as 1$^{st}$ ethanol extraction and is approximately 75% of the totals in the culture medium. For the butyl acetate extraction, the butyl acetate extract was obtained as described in Example 4. Table 3 below provides a comparison between two recovery methods. The detailed testing procedure/conditions are described as in Example 4. The solvent extracts were analyzed by reverse phase HPLC and the results are shown in Table 3 below.

TABLE 3

| Solvent and extraction method | Recovery % |
| --- | --- |
| 1st Ethanol Extraction from de-watered biomass | 75% |
| Butyl Acetate Extraction from Broth | 98% |

Example 6: Recovery of Cannabinoid by Water Reduction by Filtration and Cell Removal by Centrifugation from an Engineered Cell Culture by Method 2 and 5

Filter aid was added to the cell culture (broth) comprising cells engineered to produce one or more cannabinoids in a culture medium 0.5% (w/w) and was pressured through a dead-end microfiltration unit through a volumetric pump. The filtration unit was equipped with a polypropylene membrane with a normal pore size of 3 micrometer. Constant feed rate may be maintained until pressure difference reaches 10 psi across the membrane. In some examples, the pressure difference can be up to 60 psi. Then, the unit was drained and the wet filter cake was collected. The wet filter cake contained 98-100% of total CBGA/CBG in the broth comprising cells and the culture medium and may had a total biomass concentration of approximately 50%.

The obtained wet filter cake was subjected to an ethanol extraction as described by method 2 and 5. 100 g of the wet filter cake was mixed with 200 g of 100% ethanol at room temperature (~25° C.) and the mixture was vortexed to totally mix, disperse, and suspend the solid in 80% ethanol/water solution; the mixing continued throughout the process. Then the mixture was centrifuged at 8000 g-force for 5 min to separate liquid ethanolphase and the bottom semi solid. The top ethanol phase contained >75% of total CBGA/CBG from the wet filter cake. A second ethanol extraction followed by a subsequent centrifugation under similar conditions increased to a >95% recovery of the cannabinoid from the original cell culture medium.

Example 7: Recovery of Cannabinoid by Water Reduction by Filtration and Cell Removal by Filtration from an Engineered Cell Culture by Method 2 and 5

Filter aid was added to the cell culture (broth) comprising cells engineered to produce one or more cannabinoids in a culture medium 0.5% (w/w) and was pressured through a dead-end microfiltration unit through a volumetric pump. The filtration unit was equipped with a polypropylene membrane with a normal pore size of 3 micrometer. Constant feed rate may be maintained until pressure difference reaches 10 psi across the membrane. In some examples, the pressure difference can be up to 60 psi. Then, the unit was drained and the wet filter cake was collected. The wet filter cake contained 98-100% of total CBGA/CBG in the broth comprising cells and the culture medium and may had a total biomass concentration of approximately 50%.

The obtained wet filter cake was subjected to an ethanol extraction as described by method 2 and 5. 100 g of the wet filter cake was mixed with 200 g of 100% ethanol at room temperature (~25° C.) and the mixture was vortexed to totally mix, disperse, and suspend the solid in 80% ethanol/ water solution; the mixing continued throughout the process. Then the mixture was filtered through a dead end filtration unit. The filtration unit was equipped with a polypropylene membrane with a normal pore size of 3 micrometer. Constant feed rate was maintained until pressure difference reaches 10 psi across the membrane. In some examples, the pressure difference can reach approximately 60 psi. Filter cake was washed with additional ethanol to recover residual product in the filter cake. The ethanol wet filter cake was air purged to achieve an approximately 70% solid content in the filter cake. The filtered ethanol solution contained >99% of CBGA/CBG that was originally present in the cell culture medium comprising the cell.

We claim:

1. A method of recovering a cannabinoid from a cell culture, the method comprising:
    a) providing a cell culture comprising cells engineered to produce a cannabinoid in a culture medium;
    b) treating the culture at a temperature below the melting point of the cannabinoid to generate a first pellet comprising cells, insoluble cellular material, and the cannabinoid, and a first supernatant comprising culture medium;
    c) removing the first supernatant from the first pellet;
    d) adding a water-immiscible organic solvent to the first pellet to generate a solvent-extracted pellet mixture;
    e) separating, the solvent-extracted pellet mixture to generate a heavy phase and a light phase, wherein the light phase comprises the water-immiscible organic solvent and the cannabinoid; and
    f) recovering the light phase comprising the cannabinoid.

2. The method of claim 1 wherein step b) treating comprises separating using g-force, separating by centrifugation, filtrating, by filtration under dead end microfiltration mode, evaporating, or flocculating; wherein step e) separating comprises g-force separating or both b) and e).

3. The method according to claim 1 additionally comprising one or more of the steps:
    g) filtering the light phase;
    h) adding water to the filtered light phase, wherein added water removes water soluble impurities;
    i) separating the aqueous phase from the light phase by separation using g-force, by centrifugation.

4. The method according to claim 3, wherein filtering uses a membrane having a molecular weight cutoff in the range of 100 to 5,000 kilodaltons.

5. A method of recovering a cannabinoid from a cell culture, the method comprising:
    a) providing a cell culture comprising cells engineered to produce a cannabinoid in a culture medium;
    b) contacting the culture with a water-immiscible solvent, wherein the contacting forms a water-immiscible phase and an aqueous phase from the culture medium;
    c) separating the water-immiscible phase from the aqueous phase, wherein the water-immiscible phase comprises the cannabinoid;
    d) separating the aqueous phase from light phase by separation using g-force by centrifugation.

6. The method of claim 5 comprising one or more of the following steps:
    e) filtering the light phase;
    f) adding water to the filtered light phase, wherein added water removes water soluble impurities; and
    g) separating the aqueous phase from the light phase by separation using g-force, by centrifugation.

7. The method of claim 6, wherein step c), step g), or both steps c) and g) separating comprises separating using g-force, by centrifugation.

8. The method of claim 6 which i) performs step e) before steps f) and g); or ii) which performs step e) after steps f) and g).

9. The method of claim 6, further comprising heating the water-immiscible phase.

10. The method of claim 6, further comprising removing the water-immiscible solvent from the water-immiscible phase of step (c) and resuspending the cannabinoid in a second solvent, wherein the second solvent is optionally ethanol.

11. The method of claim 6, wherein the water-immiscible solvent is selected from the group consisting of: C4-C10 acyl ester, Anisole, Butylacetate, tert-Butylmethyl ether, Chlorobenzene, Chloroform, Cumene, Cyclohexane, 1,2-Dichloroethene, Dichloromethane, 1,2-Dimethoxyethane, 1,4-Dioxane, 2-, Ethylacetate, Ethylether, Ethylformate, Heptane, Hexane, Isobutyl acetate, Isopropylacetate, Methylacetate, 3-Methyl-1-butanol, Methylbutylketone, Methylcyclohexane, Methylethylketone, Methylisobutyl ketone, 2-Methyl-1-propanol, N-Methylpyrrolidone, Pentane, 1-Pentanol, Propylacetate, Tetralin, Toluene, 1,1,2-Trichloroethene, Triethylamine, and Xylene.

12. A method of recovering a cannabinoid from a cell culture, the method comprising:
    a) providing a cell culture comprising cells engineered to produce a cannabinoid in a culture medium;
    b) allowing the flow of at least liquid components of the cell culture through a filtration membrane wherein a retentate comprising cells and cannabinoid is collected on a portion of the filtration membrane;
    c) contacting the retentate with a solvent, wherein the solvent extracts the cannabinoid from the retentate, optionally comprising a step of separating the retentate and solvent to form a liquid phase comprising the solvent and cannabinoid and a heavy phase comprising semi-solids, solids, or a mixture thereof; and
    d) recovering the cannabinoid from the solvent.

13. The method of claim 12 wherein prior to, or during step b) a filter aid selected from the group consisting of silica, alumina, zeolites, diatomaceous earth, sand, cellulosic material, lignocellulosic material, pumice, and perlite, is added to the cell culture in an amount up to about 5% (wt).

14. The method of claim 12 wherein the filtration membrane has a normal pore size in the range of 0.2 micrometer to 20 micrometer.

15. The method of any of claim 12 wherein the retentate is contacted with an amount of solvent to provide a weight ratio of retentate:solvent in the range of 2:1 to 1:2.

16. A method of recovering a cannabinoid from a cell culture, the method comprising:
    a) removing a cell culture from a fermentation vessel, the cell culture comprising cells engineered to produce a cannabinoid in a culture medium, wherein the fermentation vessel comprises a surface that contacts the cannabinoid in the culture medium;
    b) contacting the surface of the fermentation vessel with an alkaline solution, wherein contacting removes cannabinoid from the surface.

17. The method of claim 16 wherein the alkaline solution comprises an alkali metal hydroxide, an alkaline earth metal hydroxide, or a combination thereof, wherein the alkali metal hydroxide, alkaline earth metal hydroxide, or combination thereof are optionally present at a concentration of about 0.1N or greater.

18. The method of claim 16 further comprising a step of neutralizing the alkaline solution comprising the cannabinoid, wherein neutralizing optionally comprises adding hydrochloric acid, sulfuric acid, acetic acid, nitric acid, or a combination thereof, to the alkaline solution comprising the cannabinoid, optionally comprising a step of contacting neutralized solution comprising cannabinoid with a water immiscible solvent, wherein contacting extracts the cannabinoid from the solution to the solvent.

19. The method according to claim 1 wherein the cannabinoid is selected from the group consisting of cannabichromene (CBC) type, cannabigerol (CBG) type, cannabidiol (CBD) type, Δ9-trans-tetrahydrocannabinol (Δ9-THC) type (e.g. Δ9-tetrahydrocannabinolic acid), Δ8-trans-tetrahydrocannabinol (Δ8-THC) type, cannabicyclol (CBL) type, cannabielsoin (CBE) type, cannabinol (CBN) type, cannabinodiol (CBND) type, cannabitriol (CBT) type, cannabigerolic acid (CBGA), cannabigerolic acid, monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CBD), cannabidiol monomethylether (CBDM), cannabidiol-C4 (CBD-C4), cannabidivarinic acid (CBDVA), cannabidivarin (CBDV), cannabidiorcol (CBD-C1), Δ9-tetrahydrocannabinolic acid A (THCA-A), Δ9-tetrahydrocannabinolic acid B (THCA-B), Δ9-tetrahydrocannabinol (THC), Δ9-tetrahydrocannabinolic acid-C4 (THCA-C4), Δ9-tetrahydrocannabinol-C4 (THC-C4), Δ9-tetrahydrocannabivarinic acid (THCVA), Δ9-tetrahydrocannabivarin (THCV), Δ9-tetrahydrocannabiorcolic acid (THCA-C1), Δ9-tetrahydrocannabiorcol (THC-C1), Δ7-cis-iso-tetrahydrocannabivarin, Δ8-tetrahydrocannabinolic acid (Δ8-THCA), Δ8-tetrahydrocannabinol (Δ8-THC), cannabicyclolic acid (CBLA), cannabicyclol (CBL), cannabicyclovarin (CBLV), cannabielsoic acid A (CBEA-A), cannabielsoic acid B (CBEA-B), cannabielsoin (CBE), cannabielsoinic acid, cannabicitranic acid, cannabinolic acid (CBNA), cannabinol (CBN), cannabinol methylether (CBNM), cannabinol-C4, (CBN-C4), cannabivarin (CBV), cannabinol-C2 (CNB-C2), cannabiorcol (CBN-C1), cannabinodiol (CBND), cannabinodivarin (CBVD), cannabitriol (CBT), 10-ethyoxy-9-hydroxy-delta-6a-tetrahydrocannabinol, 8,9-dihydroxyl-delta-6a-tetrahydrocannabinol, cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxy-alpha-alpha-2-trimethyl-9-n-propyl-2,6-methano-2H-1-benzoxocin-5-methanol (OH-iso-HHCV), cannabiripsol (CBR), and trihydroxy-delta-9-tetrahydrocannabinol (triOH-THC).

\* \* \* \* \*